(12) United States Patent
Stotz

(10) Patent No.: US 11,944,805 B2
(45) Date of Patent: Apr. 2, 2024

(54) PUMP FOR DELIVERING A FLUID AND METHOD OF MANUFACTURING A PUMP

(71) Applicant: KARDION GMBH, Stuttgart (DE)

(72) Inventor: Ingo Stotz, Ditzingen (DE)

(*) Notice: Subject to any disclaimer, the term of this patent is extended or adjusted under 35 U.S.C. 154(b) by 389 days.

(21) Appl. No.: 17/161,326

(22) Filed: Jan. 28, 2021

(65) Prior Publication Data
US 2021/0236803 A1     Aug. 5, 2021

(30) Foreign Application Priority Data
Jan. 31, 2020 (DE) .................. 102020102474.6

(51) Int. Cl.
   *A61M 60/827*      (2021.01)
   *A61M 60/13*       (2021.01)
   (Continued)

(52) U.S. Cl.
   CPC .......... *A61M 60/827* (2021.01); *A61M 60/13* (2021.01); *A61M 60/139* (2021.01); *A61M 60/216* (2021.01); *A61M 60/221* (2021.01); *A61M 60/408* (2021.01); *A61M 60/416* (2021.01); *A61M 60/81* (2021.01);
   (Continued)

(58) Field of Classification Search
CPC .. A61M 60/827; A61M 60/13; A61M 60/139; A61M 60/216; A61M 60/221; A61M 60/408; A61M 60/416; A61M 60/81; A61M 60/825; A61M 60/861; A61M 2207/00; F04D 7/00; F04D 29/043; F04D 29/106; F04D 29/18; F04D 29/406; F04D 29/605; F04D 29/126; F04D 29/628
See application file for complete search history.

(56) References Cited

U.S. PATENT DOCUMENTS 2,254,698 A    9/1941   Hansen, Jr.
3,085,407 A    4/1963   Tomlinson
              (Continued)

FOREIGN PATENT DOCUMENTS

AU        7993698      2/1999
AU     2002308409    12/2005
            (Continued)

OTHER PUBLICATIONS

"ABMD—Taking a Closer Look at Impella ECP as the Pivotal Trial Gets Underway", Guggenheim, Press Release, Mar. 29, 2022, pp. 4.
(Continued)

*Primary Examiner* — Courtney D Heinle
*Assistant Examiner* — Andrew J Marien
(74) *Attorney, Agent, or Firm* — Knobbe Martens Olson and Bear, LLP

(57) ABSTRACT

The approach presented here concerns a pump for delivering a fluid. The pump comprises an impeller, a drive device with a shaft, a shaft housing and a sealing device. The impeller is shaped to deliver the fluid. The drive device with the shaft is designed to drive the impeller. The shaft housing is shaped to receive the shaft and/or the drive device. The sealing device comprises at least one casing sealing element and/or an impeller sealing element which is received between the drive device and the impeller and which is designed to prevent fluid from entering the drive device and/or the shaft casing during operation of the pump.

20 Claims, 3 Drawing Sheets

(51) Int. Cl.
   *A61M 60/139* (2021.01)
   *A61M 60/216* (2021.01)
   *A61M 60/221* (2021.01)
   *A61M 60/408* (2021.01)
   *A61M 60/416* (2021.01)
   *A61M 60/81* (2021.01)
   *A61M 60/825* (2021.01)
   *A61M 60/861* (2021.01)
   *F04D 7/00* (2006.01)
   *F04D 29/043* (2006.01)
   *F04D 29/10* (2006.01)
   *F04D 29/18* (2006.01)
   *F04D 29/40* (2006.01)
   *F04D 29/60* (2006.01)

(52) U.S. Cl.
   CPC ........ *A61M 60/825* (2021.01); *A61M 60/861* (2021.01); *F04D 7/00* (2013.01); *F04D 29/043* (2013.01); *F04D 29/106* (2013.01); *F04D 29/18* (2013.01); *F04D 29/406* (2013.01); *F04D 29/605* (2013.01); *A61M 2207/00* (2013.01)

(56) References Cited

U.S. PATENT DOCUMENTS

| | | |
|---|---|---|
| 3,505,987 A | 4/1970 | Heilman |
| 3,568,659 A | 3/1971 | Karnegis |
| 3,614,181 A | 10/1971 | Meeks |
| 3,747,998 A | 7/1973 | Klein et al. |
| 3,807,813 A | 4/1974 | Milligan |
| 3,995,617 A | 12/1976 | Watkins et al. |
| 4,115,040 A | 9/1978 | Knorr |
| 4,471,252 A | 9/1984 | West |
| 4,625,712 A | 12/1986 | Wampler |
| 4,643,641 A | 2/1987 | Clausen et al. |
| 4,753,221 A | 6/1988 | Kensey et al. |
| 4,779,614 A | 10/1988 | Moise |
| 4,785,795 A | 11/1988 | Singh et al. |
| 4,817,586 A | 4/1989 | Wampler |
| 4,846,152 A * | 7/1989 | Wampler ............ A61M 60/237 600/16 |
| 4,888,011 A | 12/1989 | Kung et al. |
| 4,889,131 A | 12/1989 | Salem et al. |
| 4,895,557 A | 1/1990 | Moise et al. |
| 4,896,754 A | 1/1990 | Carlson et al. |
| 4,902,272 A | 2/1990 | Milder et al. |
| 4,908,012 A | 3/1990 | Moise et al. |
| 4,927,407 A | 5/1990 | Dorman |
| 4,943,275 A | 7/1990 | Stricker |
| 4,944,722 A | 7/1990 | Carriker et al. |
| 4,968,300 A | 11/1990 | Moutafis et al. |
| 4,985,014 A | 1/1991 | Orejola |
| 5,044,897 A | 9/1991 | Dorman |
| 5,061,256 A | 10/1991 | Wampler |
| 5,089,016 A | 2/1992 | Millner et al. |
| 5,090,957 A | 2/1992 | Moutafis et al. |
| 5,112,292 A | 5/1992 | Hwang et al. |
| 5,112,349 A | 5/1992 | Summers et al. |
| 5,116,305 A | 5/1992 | Milder et al. |
| 5,195,877 A | 3/1993 | Kletschka |
| 5,297,940 A | 3/1994 | Buse |
| 5,313,765 A | 5/1994 | Martin |
| 5,344,443 A | 9/1994 | Palma et al. |
| 5,354,271 A | 10/1994 | Voda |
| 5,376,114 A * | 12/1994 | Jarvik ................ A61M 60/861 623/3.13 |
| 5,399,145 A | 3/1995 | Ito et al. |
| 5,405,383 A | 4/1995 | Barr |
| 5,443,503 A | 8/1995 | Yamane |
| 5,456,715 A | 10/1995 | Liotta |
| 5,527,159 A | 6/1996 | Bozeman, Jr. et al. |
| 5,599,173 A | 2/1997 | Chen et al. |
| 5,613,935 A | 3/1997 | Jarvik |
| 5,695,471 A | 12/1997 | Wampler |
| 5,720,771 A | 2/1998 | Snell |
| 5,746,709 A | 5/1998 | Rom et al. |
| 5,749,855 A | 5/1998 | Reitan |
| 5,752,976 A | 5/1998 | Duffin et al. |
| 5,766,207 A | 6/1998 | Potter et al. |
| 5,831,365 A | 11/1998 | Keim et al. |
| 5,888,241 A | 3/1999 | Jarvik |
| 5,888,242 A | 3/1999 | Antaki et al. |
| 5,904,646 A | 5/1999 | Jarvik |
| 5,911,685 A * | 6/1999 | Siess ..................... F04D 29/047 600/16 |
| 5,921,913 A | 7/1999 | Siess |
| 5,964,694 A * | 10/1999 | Siess ................... A61M 60/416 623/3.1 |
| 6,001,056 A | 12/1999 | Jassawalla et al. |
| 6,007,478 A | 12/1999 | Siess et al. |
| 6,018,208 A | 1/2000 | Maher et al. |
| 6,050,975 A | 4/2000 | Poirier |
| 6,071,093 A | 6/2000 | Hart |
| 6,116,862 A | 9/2000 | Rau et al. |
| 6,123,659 A | 9/2000 | le Blanc et al. |
| 6,135,710 A | 10/2000 | Araki et al. |
| 6,149,405 A | 11/2000 | Abe et al. |
| 6,155,969 A | 12/2000 | Schima et al. |
| 6,158,984 A | 12/2000 | Cao et al. |
| 6,161,838 A | 12/2000 | Balsells |
| 6,176,848 B1 | 1/2001 | Rau et al. |
| 6,186,665 B1 | 2/2001 | Maher et al. |
| 6,210,318 B1 | 4/2001 | Lederman |
| 6,217,541 B1 | 4/2001 | Yu |
| 6,220,832 B1 | 4/2001 | Schob |
| 6,227,820 B1 | 5/2001 | Jarvik |
| 6,245,007 B1 | 6/2001 | Bedingham et al. |
| 6,254,359 B1 | 7/2001 | Aber |
| 6,264,205 B1 | 7/2001 | Balsells |
| 6,264,601 B1 | 7/2001 | Jassawalla et al. |
| 6,264,645 B1 | 7/2001 | Jonkman |
| 6,293,752 B1 | 9/2001 | Clague et al. |
| 6,351,048 B1 | 2/2002 | Schob et al. |
| 6,361,292 B1 | 3/2002 | Chang et al. |
| 6,432,136 B1 | 8/2002 | Weiss et al. |
| 6,445,956 B1 | 9/2002 | Laird et al. |
| 6,447,266 B2 | 9/2002 | Antaki et al. |
| 6,527,698 B1 | 3/2003 | Kung et al. |
| 6,530,876 B1 | 3/2003 | Spence |
| 6,533,716 B1 | 3/2003 | Schmitz-Rode et al. |
| 6,540,658 B1 | 4/2003 | Fasciano et al. |
| 6,544,216 B1 | 4/2003 | Sammler et al. |
| 6,579,257 B1 | 6/2003 | Elgas et al. |
| 6,592,620 B1 | 7/2003 | Lancisi et al. |
| 6,595,743 B1 | 7/2003 | Kazatchkov et al. |
| 6,623,475 B1 | 9/2003 | Siess |
| 6,719,791 B1 | 4/2004 | Nüsser et al. |
| 6,794,789 B2 | 9/2004 | Siess et al. |
| 6,841,910 B2 | 1/2005 | Gery |
| 6,879,126 B2 | 4/2005 | Paden et al. |
| 6,912,423 B2 | 6/2005 | Ley et al. |
| 6,942,611 B2 | 9/2005 | Siess |
| 6,949,066 B2 | 9/2005 | Bearnson et al. |
| 6,969,345 B2 | 11/2005 | Jassawalla et al. |
| 7,011,620 B1 * | 3/2006 | Siess .................... A61M 60/13 600/16 |
| 7,014,620 B2 * | 3/2006 | Kim ................... A61H 15/0078 601/99 |
| 7,022,100 B1 | 4/2006 | Aboul-Hosn et al. |
| 7,027,875 B2 | 4/2006 | Siess et al. |
| 7,070,398 B2 | 7/2006 | Olsen et al. |
| 7,070,555 B2 | 7/2006 | Siess |
| 7,083,588 B1 | 8/2006 | Shmulewitz et al. |
| 7,144,364 B2 | 12/2006 | Barbut et al. |
| 7,160,243 B2 | 1/2007 | Medvedev |
| 7,238,151 B2 | 7/2007 | Frazier |
| 7,241,257 B1 | 7/2007 | Ainsworth et al. |
| 7,264,606 B2 | 9/2007 | Jarvik et al. |
| 7,393,181 B2 | 7/2008 | McBride et al. |
| 7,462,019 B1 | 12/2008 | Allarie et al. |
| 7,479,102 B2 | 1/2009 | Jarvik |

(56) References Cited

U.S. PATENT DOCUMENTS

| | | |
|---|---|---|
| 7,502,648 B2 | 3/2009 | Okubo et al. |
| 7,736,296 B2 | 6/2010 | Siess et al. |
| 7,762,941 B2 | 7/2010 | Jarvik |
| 7,798,952 B2 | 9/2010 | Tansley et al. |
| 7,841,976 B2 | 11/2010 | McBride et al. |
| 7,850,593 B2 | 12/2010 | Vincent et al. |
| 7,878,967 B1 | 2/2011 | Khanal |
| 7,934,909 B2 | 2/2011 | Jenson |
| 7,914,436 B1 | 3/2011 | Kung |
| 7,959,551 B2 | 6/2011 | Jarvik |
| 7,963,905 B2 | 6/2011 | Salmonsen et al. |
| 7,998,190 B2 | 8/2011 | Gharib et al. |
| 8,012,079 B2 | 9/2011 | Delgado, III |
| 8,075,472 B2 | 12/2011 | Zilbershlag et al. |
| 8,088,059 B2 | 1/2012 | Jarvik |
| 8,114,008 B2 | 2/2012 | Hidaka et al. |
| 8,123,669 B2 | 2/2012 | Siess et al. |
| RE43,299 E | 4/2012 | Siess |
| 8,152,845 B2 | 4/2012 | Bourque |
| 8,177,703 B2 | 5/2012 | Smith et al. |
| 8,216,122 B2 | 7/2012 | Kung |
| 8,371,997 B2 | 2/2013 | Shifflette |
| 8,376,926 B2 | 2/2013 | Benkowsi et al. |
| 8,382,695 B1 | 2/2013 | Patel |
| 8,388,565 B2 | 3/2013 | Shifflette |
| 8,419,609 B2 | 4/2013 | Shambaugh, Jr. et al. |
| 8,449,443 B2 | 5/2013 | Rodefeld et al. |
| 8,480,555 B2 | 7/2013 | Kung |
| 8,485,961 B2 | 7/2013 | Campbell et al. |
| 8,512,012 B2 | 8/2013 | Akdis et al. |
| 8,535,211 B2 | 9/2013 | Campbell et al. |
| 8,545,380 B2 | 10/2013 | Farnan et al. |
| 8,562,508 B2 | 10/2013 | Dague et al. |
| 8,585,572 B2 | 11/2013 | Mehmanesh |
| 8,591,393 B2 | 11/2013 | Walters et al. |
| 8,591,538 B2 | 11/2013 | Gellman |
| 8,591,539 B2 | 11/2013 | Gellman |
| 8,597,170 B2 | 12/2013 | Walters et al. |
| 8,617,239 B2 | 12/2013 | Reitan |
| 8,622,949 B2 | 1/2014 | Zafirelis et al. |
| 8,641,594 B2 | 2/2014 | LaRose et al. |
| 8,657,875 B2 | 2/2014 | Kung et al. |
| 8,684,362 B2 | 4/2014 | Balsells et al. |
| 8,684,904 B2 | 4/2014 | Campbell et al. |
| 8,690,749 B1 | 4/2014 | Nunez |
| 8,721,517 B2 | 5/2014 | Zeng et al. |
| 8,727,959 B2 | 5/2014 | Reitan et al. |
| 8,731,664 B2 | 5/2014 | Foster et al. |
| 8,734,331 B2 | 5/2014 | Evans et al. |
| 8,814,933 B2 | 8/2014 | Siess |
| 8,849,398 B2 | 9/2014 | Evans |
| 8,864,642 B2 | 10/2014 | Scheckel |
| 8,864,643 B2 | 10/2014 | Reichenbach et al. |
| 8,864,644 B2 | 10/2014 | Yomtov |
| 8,882,477 B2 | 11/2014 | Fritz, IV et al. |
| 8,888,728 B2 | 11/2014 | Aboul-Hosn et al. |
| 8,894,387 B2 | 11/2014 | White |
| 8,897,873 B2 | 11/2014 | Schima et al. |
| 8,900,060 B2 | 12/2014 | Liebing |
| 8,900,115 B2 | 12/2014 | Bolling et al. |
| 8,932,246 B2 | 1/2015 | Ferrari |
| 8,992,406 B2 | 3/2015 | Corbett |
| 8,992,407 B2 | 3/2015 | Smith et al. |
| 9,028,216 B2 | 5/2015 | Schumacher et al. |
| 9,028,392 B2 | 5/2015 | Shifflette |
| 9,033,863 B2 | 5/2015 | Jarvik |
| 9,091,271 B2 | 7/2015 | Bourque |
| 9,138,518 B2 | 9/2015 | Campbell et al. |
| 9,144,638 B2 | 9/2015 | Zimmermann et al. |
| 9,162,017 B2 | 10/2015 | Evans et al. |
| 9,192,705 B2 | 11/2015 | Yanai et al. |
| 9,199,020 B2 | 12/2015 | Siess |
| 9,265,870 B2 | 2/2016 | Reichenbach et al. |
| 9,297,735 B2 | 3/2016 | Graichen et al. |
| 9,314,556 B2 | 4/2016 | Tuseth |
| 9,327,067 B2 | 5/2016 | Zeng et al. |
| 9,327,068 B2 | 5/2016 | Aboul-Hosn et al. |
| 9,345,824 B2 | 5/2016 | Mohl et al. |
| 9,370,613 B2 | 6/2016 | Hsu et al. |
| 9,371,826 B2 | 6/2016 | Yanai et al. |
| 9,381,286 B2 | 7/2016 | Spence et al. |
| 9,421,311 B2 | 8/2016 | Tanner et al. |
| 9,433,713 B2 | 9/2016 | Corbett et al. |
| 9,440,013 B2 | 9/2016 | Dowling et al. |
| 9,486,566 B2 | 11/2016 | Siess |
| 9,492,601 B2 | 11/2016 | Casas et al. |
| 9,533,084 B2 | 1/2017 | Siess et al. |
| 9,539,378 B2 | 1/2017 | Tuseth |
| 9,550,017 B2 | 1/2017 | Spanier et al. |
| 9,555,173 B2 | 1/2017 | Spanier |
| 9,555,175 B2 | 1/2017 | Bulent et al. |
| 9,556,873 B2 | 1/2017 | Yanai et al. |
| 9,561,313 B2 | 2/2017 | Taskin |
| 9,579,433 B2 | 2/2017 | LaRose et al. |
| 9,585,991 B2 | 3/2017 | Spence |
| 9,592,397 B2 | 3/2017 | Hansen et al. |
| 9,616,157 B2 | 4/2017 | Akdis |
| 9,623,162 B2 | 4/2017 | Graham et al. |
| 9,623,163 B1 | 4/2017 | Fischi |
| 9,636,442 B2 | 5/2017 | Karmon et al. |
| 9,669,144 B2 | 6/2017 | Spanier et al. |
| 9,675,738 B2 | 6/2017 | Tanner et al. |
| 9,675,739 B2 | 6/2017 | Tanner et al. |
| 9,675,740 B2 | 6/2017 | Zeng et al. |
| 9,682,180 B2 | 6/2017 | Hoarau et al. |
| 9,731,058 B2 | 8/2017 | Siebenhaar et al. |
| 9,759,222 B2 | 9/2017 | Zimmermann et al. |
| 9,770,543 B2 | 9/2017 | Tanner et al. |
| 9,789,238 B2 | 10/2017 | Aboul-Hosn et al. |
| 9,801,990 B2 | 10/2017 | Lynch |
| 9,814,813 B2 | 11/2017 | Corbett |
| 9,821,100 B2 | 11/2017 | Corbett et al. |
| 9,833,550 B2 | 12/2017 | Siess |
| 9,849,223 B2 | 12/2017 | LaRose |
| 9,872,948 B2 | 1/2018 | Siess |
| 9,878,087 B2 | 1/2018 | Richardson et al. |
| 9,907,890 B2 | 3/2018 | Muller |
| 9,919,087 B2 | 3/2018 | Pfeffer et al. |
| 9,950,101 B2 | 4/2018 | Smith et al. |
| 9,968,719 B2 | 5/2018 | Colella |
| 9,999,714 B2 | 6/2018 | Spanier et al. |
| 10,029,037 B2 | 7/2018 | Muller et al. |
| 10,123,875 B2 | 11/2018 | Wildhirt et al. |
| 10,124,102 B2 | 11/2018 | Bulent et al. |
| 10,130,742 B2 | 11/2018 | Tuseth |
| 10,149,932 B2 | 12/2018 | McBride et al. |
| 10,179,197 B2 | 1/2019 | Kaiser et al. |
| 10,201,645 B2 | 2/2019 | Muller |
| 10,207,038 B2 | 2/2019 | Neumann |
| 10,220,129 B2 | 3/2019 | Ayre et al. |
| 10,232,099 B2 | 3/2019 | Peters et al. |
| 10,238,782 B2 | 3/2019 | Barry |
| 10,238,783 B2 | 3/2019 | Aboul-Hosn et al. |
| 10,251,986 B2 | 4/2019 | Larose et al. |
| 10,279,093 B2 | 5/2019 | Reichenbach et al. |
| 10,293,090 B2 | 5/2019 | Bonde et al. |
| 10,300,185 B2 | 5/2019 | Aboul-Hosn et al. |
| 10,300,249 B2 | 5/2019 | Tao et al. |
| 10,322,217 B2 | 6/2019 | Spence |
| 10,342,906 B2 | 7/2019 | D'Ambrosio et al. |
| 10,357,598 B2 | 7/2019 | Aboul-Hosn et al. |
| 10,361,617 B2 | 7/2019 | Mueller et al. |
| 10,371,150 B2 | 8/2019 | Wu et al. |
| 10,376,162 B2 | 8/2019 | Edelman et al. |
| 10,420,869 B2 | 9/2019 | Cornen |
| 10,434,232 B2 | 10/2019 | Wu et al. |
| 10,449,275 B2 | 10/2019 | Corbett |
| 10,449,279 B2 | 10/2019 | Muller |
| 10,478,538 B2 | 11/2019 | Scheckel et al. |
| 10,478,539 B2 | 11/2019 | Pfeffer et al. |
| 10,478,542 B2 | 11/2019 | Jahangir |
| 10,500,323 B2 | 12/2019 | Heuring et al. |
| 10,512,537 B2 | 12/2019 | Corbett et al. |
| 10,525,178 B2 | 1/2020 | Zeng |

(56) References Cited

U.S. PATENT DOCUMENTS

| | | | |
|---|---|---|---|
| 10,537,670 B2 | 1/2020 | Tuseth et al. |
| 10,537,672 B2 | 1/2020 | Tuseth et al. |
| 10,557,475 B2 | 2/2020 | Roehn |
| 10,561,771 B2 | 2/2020 | Heilman et al. |
| 10,561,772 B2 | 2/2020 | Schumacher |
| 10,576,191 B2 | 3/2020 | LaRose |
| 10,584,589 B2 | 3/2020 | Schumacher et al. |
| 10,589,012 B2 | 3/2020 | Toellner et al. |
| 10,589,013 B2 | 3/2020 | Bourque |
| 10,610,626 B2 | 4/2020 | Spanier et al. |
| 10,617,808 B2 | 4/2020 | Hastie et al. |
| 10,632,241 B2 | 4/2020 | Schenck et al. |
| 10,660,998 B2 * | 5/2020 | Hodges ............ A61M 60/422 |
| 10,662,967 B2 | 5/2020 | Scheckel |
| 10,668,195 B2 | 6/2020 | Flores |
| 10,669,855 B2 | 6/2020 | Toellner et al. |
| 10,722,631 B2 | 7/2020 | Salahieh et al. |
| 10,814,053 B2 | 10/2020 | Throckmorton et al. |
| 10,857,273 B2 | 12/2020 | Hodges et al. |
| 11,033,729 B2 | 6/2021 | Scheckel et al. |
| 11,045,638 B2 | 6/2021 | Keenan et al. |
| 11,058,863 B2 | 7/2021 | Demou |
| 11,058,865 B2 | 7/2021 | Fitzgerald et al. |
| 11,065,434 B2 | 7/2021 | Egler et al. |
| 11,092,158 B2 | 8/2021 | Siess et al. |
| 11,097,092 B2 | 8/2021 | Siess et al. |
| 11,103,689 B2 | 8/2021 | Siess et al. |
| 11,103,690 B2 | 8/2021 | Epple |
| 11,107,626 B2 | 8/2021 | Siess et al. |
| 11,123,538 B2 | 9/2021 | Epple et al. |
| 11,123,539 B2 | 9/2021 | Pfeffer et al. |
| 11,123,541 B2 | 9/2021 | Corbett et al. |
| 11,129,978 B2 | 9/2021 | Pfeffer et al. |
| 11,141,579 B2 | 10/2021 | Steingräber |
| 11,160,970 B2 | 11/2021 | Muller et al. |
| 11,167,124 B2 | 11/2021 | Pfeffer et al. |
| 11,173,297 B2 | 11/2021 | Muller |
| 11,179,557 B2 | 11/2021 | Georges et al. |
| 11,185,678 B2 | 11/2021 | Smith et al. |
| 11,185,680 B2 | 11/2021 | Tuval et al. |
| 11,191,944 B2 | 12/2021 | Tuval et al. |
| 11,197,989 B2 | 12/2021 | Arslan et al. |
| 11,202,901 B2 | 12/2021 | Barry |
| 11,219,756 B2 | 1/2022 | Tanner et al. |
| 11,229,786 B2 | 1/2022 | Zeng et al. |
| 11,235,138 B2 | 2/2022 | Gross-Hardt et al. |
| 11,235,140 B2 | 2/2022 | Siess et al. |
| 11,241,568 B2 | 2/2022 | Keenan et al. |
| 11,241,569 B2 | 2/2022 | Delgado, III |
| 11,253,693 B2 | 2/2022 | Pfeffer et al. |
| 11,260,212 B2 | 3/2022 | Tuval et al. |
| 11,260,213 B2 | 3/2022 | Zeng et al. |
| 11,260,215 B2 | 3/2022 | Scheckel et al. |
| 11,273,300 B2 | 3/2022 | Schafir |
| 11,273,301 B2 | 3/2022 | Pfeffer et al. |
| 11,278,711 B2 | 3/2022 | Liebing |
| 11,280,345 B2 | 3/2022 | Bredenbreuker et al. |
| 11,285,309 B2 | 3/2022 | Tuval et al. |
| 11,291,824 B2 | 4/2022 | Schwammenthal et al. |
| 11,291,825 B2 | 4/2022 | Tuval et al. |
| 11,291,826 B2 | 4/2022 | Tuval et al. |
| 11,298,519 B2 | 4/2022 | Josephy et al. |
| 11,298,520 B2 | 4/2022 | Schwammenthal et al. |
| 11,298,521 B2 | 4/2022 | Schwammenthal et al. |
| 11,298,523 B2 | 4/2022 | Tuval et al. |
| 11,298,524 B2 | 4/2022 | El Katerji et al. |
| 11,298,525 B2 | 4/2022 | Jahangir |
| 11,305,103 B2 | 4/2022 | Larose et al. |
| 11,305,105 B2 | 4/2022 | Corbett et al. |
| 11,311,711 B2 | 4/2022 | Casas et al. |
| 11,311,712 B2 | 4/2022 | Zeng et al. |
| 11,313,228 B2 | 4/2022 | Schumacher et al. |
| D951,435 S | 5/2022 | Motomura et al. |
| 11,318,295 B2 | 5/2022 | Reyes et al. |
| 11,324,940 B2 | 5/2022 | Earles et al. |
| 11,324,941 B2 | 5/2022 | Xu et al. |
| 11,331,465 B2 | 5/2022 | Epple |
| 11,331,466 B2 | 5/2022 | Keen et al. |
| 11,331,467 B2 | 5/2022 | King et al. |
| 11,331,470 B2 | 5/2022 | Muller et al. |
| 11,338,124 B2 | 5/2022 | Pfeffer et al. |
| 11,338,125 B2 | 5/2022 | Liu et al. |
| 11,344,716 B2 | 5/2022 | Taskin |
| 11,344,717 B2 | 5/2022 | Kallenbach et al. |
| 11,351,359 B2 | 6/2022 | Clifton et al. |
| 11,357,967 B2 | 6/2022 | Zeng et al. |
| 11,364,373 B2 | 6/2022 | Corbett et al. |
| 11,368,081 B2 | 6/2022 | Vogt et al. |
| 11,369,785 B2 | 6/2022 | Callaway et al. |
| 11,369,786 B2 | 6/2022 | Menon et al. |
| 11,389,639 B2 | 7/2022 | Casas |
| 11,389,641 B2 | 7/2022 | Nguyen et al. |
| 11,413,443 B2 | 8/2022 | Hodges et al. |
| 11,413,446 B2 | 8/2022 | Siess et al. |
| 11,415,150 B2 | 8/2022 | Richert et al. |
| 11,421,701 B2 | 8/2022 | Schumacher et al. |
| 11,428,236 B2 | 8/2022 | McBride et al. |
| 11,433,168 B2 | 9/2022 | Wu et al. |
| 11,434,921 B2 | 9/2022 | McBride et al. |
| 11,434,922 B2 | 9/2022 | Roehn |
| 11,446,481 B2 | 9/2022 | Wolman et al. |
| 11,446,482 B2 | 9/2022 | Kirchhoff et al. |
| 11,452,859 B2 | 9/2022 | Earles et al. |
| 11,460,030 B2 | 10/2022 | Shambaugh et al. |
| 11,471,662 B2 | 10/2022 | Akkerman et al. |
| 11,471,663 B2 | 10/2022 | Tuval et al. |
| 11,471,665 B2 | 10/2022 | Clifton et al. |
| 11,478,627 B2 | 10/2022 | Siess et al. |
| 11,478,628 B2 | 10/2022 | Muller et al. |
| 11,478,629 B2 | 10/2022 | Harjes et al. |
| 11,484,698 B2 | 11/2022 | Radman |
| 11,484,699 B2 | 11/2022 | Tuval et al. |
| 11,486,400 B2 | 11/2022 | Schumacher |
| 11,491,320 B2 | 11/2022 | Siess |
| 11,491,322 B2 | 11/2022 | Muller et al. |
| 11,497,896 B2 | 11/2022 | Tanner et al. |
| 11,497,906 B2 | 11/2022 | Grace et al. |
| 11,511,101 B2 | 11/2022 | Hastie et al. |
| 11,511,103 B2 | 11/2022 | Salahieh et al. |
| 11,511,104 B2 | 11/2022 | Dur et al. |
| 11,517,726 B2 | 12/2022 | Siess et al. |
| 11,517,736 B2 | 12/2022 | Earles et al. |
| 11,517,737 B2 | 12/2022 | Struthers et al. |
| 11,517,738 B2 | 12/2022 | Wisniewski |
| 11,517,739 B2 | 12/2022 | Toellner |
| 11,517,740 B2 | 12/2022 | Agarwa et al. |
| 11,524,137 B2 | 12/2022 | Jahangir |
| 11,524,165 B2 | 12/2022 | Tan et al. |
| 11,529,062 B2 | 12/2022 | Moyer et al. |
| 11,534,596 B2 | 12/2022 | Schafir et al. |
| 11,565,103 B2 | 1/2023 | Farago et al. |
| 11,569,015 B2 | 1/2023 | Mourran et al. |
| 11,577,067 B2 | 2/2023 | Breidall et al. |
| 11,577,068 B2 | 2/2023 | Spence et al. |
| 11,583,659 B2 | 2/2023 | Pfeffer et al. |
| 11,583,670 B2 | 2/2023 | Pfeifer et al. |
| 11,583,671 B2 | 2/2023 | Nguyen et al. |
| 11,583,672 B2 | 2/2023 | Weber et al. |
| 11,590,336 B2 | 2/2023 | Harjes et al. |
| 11,590,337 B2 | 2/2023 | Granegger et al. |
| 11,590,338 B2 | 2/2023 | Barry |
| 11,592,028 B2 | 2/2023 | Schumacher et al. |
| 11,596,727 B2 | 3/2023 | Siess et al. |
| 11,602,627 B2 | 3/2023 | Leonhardt |
| 11,617,876 B2 | 4/2023 | Scheckel et al. |
| 11,628,293 B2 | 4/2023 | Gandhi et al. |
| 11,632,015 B2 | 4/2023 | Sconzert et al. |
| 11,633,586 B2 | 4/2023 | Tanner et al. |
| 11,638,813 B2 | 5/2023 | West |
| 11,639,722 B2 | 5/2023 | Medvedev et al. |
| 11,642,511 B2 | 5/2023 | Delgado, III |
| 11,648,387 B2 | 5/2023 | Schwammenthal et al. |
| 11,648,388 B2 | 5/2023 | Siess et al. |
| 11,648,389 B2 | 5/2023 | Wang et al. |

(56) References Cited

U.S. PATENT DOCUMENTS

| | | |
|---|---|---|
| 11,648,390 B2 | 5/2023 | Spanier et al. |
| 11,648,391 B2 | 5/2023 | Schwammenthal et al. |
| 11,648,392 B2 | 5/2023 | Tuval et al. |
| 11,648,393 B2 | 5/2023 | Taskin et al. |
| 11,654,273 B2 | 5/2023 | Granegger et al. |
| 11,654,275 B2 | 5/2023 | Brandt |
| 11,654,276 B2 | 5/2023 | Fitzgerald et al. |
| 11,660,441 B2 | 5/2023 | Fitzgerald et al. |
| 11,666,747 B2 | 6/2023 | Tuval et al. |
| 11,666,748 B2 | 6/2023 | Kronstedt et al. |
| 11,668,321 B2 | 6/2023 | Richert et al. |
| 11,679,234 B2 | 6/2023 | King et al. |
| 11,679,249 B2 | 6/2023 | Scheckel et al. |
| 11,684,275 B2 | 6/2023 | Tuval et al. |
| 11,684,769 B2 | 6/2023 | Harjes et al. |
| 11,690,521 B2 | 7/2023 | Tuval et al. |
| 11,690,996 B2 | 7/2023 | Siess et al. |
| 11,697,016 B2 | 7/2023 | Epple |
| 11,701,510 B2 | 7/2023 | Demou |
| 11,702,938 B2 | 7/2023 | Schumacher et al. |
| 11,703,064 B2 | 7/2023 | Bredenbreuker et al. |
| 11,708,833 B2 | 7/2023 | McBride et al. |
| 11,746,906 B1 | 9/2023 | Balta et al. |
| 11,754,075 B2 | 9/2023 | Schuelke et al. |
| 11,759,622 B2 | 9/2023 | Siess et al. |
| 11,804,767 B2 | 10/2023 | Vogt et al. |
| 2001/0009645 A1 | 7/2001 | Noda |
| 2001/0041934 A1* | 11/2001 | Yamazaki ........... A61M 60/174 623/3.13 |
| 2002/0147495 A1 | 10/2002 | Petroff |
| 2002/0153664 A1 | 10/2002 | Schroeder |
| 2003/0091450 A1 | 5/2003 | Davis et al. |
| 2003/0111800 A1 | 6/2003 | Kreutzer |
| 2003/0139643 A1 | 7/2003 | Smith et al. |
| 2003/0191357 A1 | 10/2003 | Frazier |
| 2004/0102674 A1 | 5/2004 | Zadini et al. |
| 2004/0115038 A1 | 6/2004 | Nuesser et al. |
| 2004/0167376 A1 | 8/2004 | Peters et al. |
| 2004/0234391 A1 | 11/2004 | Izraelev |
| 2004/0241019 A1 | 12/2004 | Goldowsky |
| 2004/0260346 A1 | 12/2004 | Overall et al. |
| 2005/0006083 A1 | 1/2005 | Chen et al. |
| 2005/0019167 A1 | 1/2005 | Nusser et al. |
| 2005/0085683 A1 | 4/2005 | Bolling et al. |
| 2005/0220636 A1 | 10/2005 | Henein et al. |
| 2006/0030809 A1 | 2/2006 | Barzilay et al. |
| 2006/0062672 A1 | 3/2006 | McBride et al. |
| 2006/0155158 A1 | 7/2006 | Aboul-Hosn |
| 2006/0224110 A1 | 10/2006 | Scott et al. |
| 2006/0276682 A1 | 12/2006 | Bolling et al. |
| 2007/0004959 A1 | 1/2007 | Carrier et al. |
| 2007/0142696 A1 | 6/2007 | Crosby et al. |
| 2007/0156006 A1 | 7/2007 | Smith et al. |
| 2008/0015517 A1 | 1/2008 | Geistert et al. |
| 2008/0058925 A1 | 3/2008 | Cohen |
| 2008/0086027 A1 | 4/2008 | Siess et al. |
| 2008/0114339 A1 | 5/2008 | McBride et al. |
| 2008/0262289 A1 | 10/2008 | Goldowsky |
| 2008/0292478 A1 | 11/2008 | Baykut et al. |
| 2009/0004037 A1 | 1/2009 | Ito |
| 2009/0112312 A1 | 4/2009 | Larose et al. |
| 2009/0203957 A1 | 8/2009 | LaRose et al. |
| 2009/0204205 A1 | 8/2009 | Larose et al. |
| 2010/0041939 A1 | 2/2010 | Siess |
| 2010/0082099 A1 | 4/2010 | Vodermayer et al. |
| 2010/0191035 A1 | 7/2010 | Kang et al. |
| 2010/0298625 A1 | 11/2010 | Reichenbach et al. |
| 2011/0184224 A1 | 7/2011 | Garrigue |
| 2011/0230821 A1 | 9/2011 | Babic |
| 2011/0237863 A1 | 9/2011 | Ricci et al. |
| 2011/0238172 A1 | 9/2011 | Akdis |
| 2012/0088954 A1 | 4/2012 | Foster |
| 2012/0093628 A1 | 4/2012 | Liebing |
| 2012/0134793 A1 | 5/2012 | Wu et al. |
| 2012/0172655 A1 | 7/2012 | Campbell et al. |
| 2012/0178986 A1 | 7/2012 | Campbell et al. |
| 2012/0247200 A1 | 10/2012 | Ahonen et al. |
| 2012/0283506 A1 | 11/2012 | Meister et al. |
| 2012/0310036 A1 | 12/2012 | Peters et al. |
| 2013/0085318 A1 | 4/2013 | Toellner |
| 2013/0209292 A1 | 8/2013 | Baykut et al. |
| 2013/0281761 A1 | 10/2013 | Kapur |
| 2013/0289376 A1 | 10/2013 | Lang |
| 2013/0303830 A1 | 11/2013 | Zeng et al. |
| 2013/0303831 A1 | 11/2013 | Evans |
| 2013/0303832 A1 | 11/2013 | Wampler |
| 2013/0330219 A1 | 12/2013 | LaRose et al. |
| 2014/0005467 A1 | 1/2014 | Farnan et al. |
| 2014/0051908 A1 | 2/2014 | Khanal et al. |
| 2014/0079557 A1 | 3/2014 | LaRose et al. |
| 2014/0167545 A1 | 6/2014 | Bremner et al. |
| 2014/0194717 A1 | 7/2014 | Wildhirt et al. |
| 2014/0200389 A1 | 7/2014 | Yanai et al. |
| 2014/0207232 A1 | 7/2014 | Garrigue |
| 2014/0275721 A1 | 9/2014 | Yanai et al. |
| 2014/0330069 A1 | 11/2014 | Hastings et al. |
| 2014/0341726 A1 | 11/2014 | Wu et al. |
| 2015/0031936 A1 | 1/2015 | LaRose et al. |
| 2015/0051438 A1 | 2/2015 | Taskin |
| 2015/0099923 A1 | 4/2015 | Magovern et al. |
| 2015/0190092 A1 | 7/2015 | Mori |
| 2015/0273184 A1 | 10/2015 | Scott et al. |
| 2015/0290372 A1 | 10/2015 | Muller et al. |
| 2015/0290373 A1 | 10/2015 | Rudser et al. |
| 2015/0306291 A1 | 10/2015 | Bonde et al. |
| 2015/0343179 A1 | 12/2015 | Schumacher et al. |
| 2015/0365738 A1 | 12/2015 | Purvis et al. |
| 2016/0008531 A1 | 1/2016 | Wang et al. |
| 2016/0038663 A1 | 2/2016 | Taskin et al. |
| 2016/0045654 A1 | 2/2016 | Connor |
| 2016/0144089 A1 | 5/2016 | Woo et al. |
| 2016/0144166 A1 | 5/2016 | Decré et al. |
| 2016/0166747 A1 | 6/2016 | Frazier et al. |
| 2016/0213828 A1 | 7/2016 | Sievers |
| 2016/0223086 A1 | 8/2016 | Balsells et al. |
| 2016/0279311 A1 | 9/2016 | Cecere et al. |
| 2016/0367739 A1 | 12/2016 | Wiesener et al. |
| 2016/0375187 A1 | 12/2016 | Lee et al. |
| 2017/0021069 A1 | 1/2017 | Hodges |
| 2017/0021074 A1 | 1/2017 | Opfermann et al. |
| 2017/0035952 A1 | 2/2017 | Muller |
| 2017/0049947 A1 | 2/2017 | Corbett et al. |
| 2017/0080136 A1 | 3/2017 | Janeczek et al. |
| 2017/0087286 A1 | 3/2017 | Spanier et al. |
| 2017/0087288 A1 | 3/2017 | Groß-HardtTim et al. |
| 2017/0128644 A1 | 5/2017 | Foster |
| 2017/0136225 A1 | 5/2017 | Siess et al. |
| 2017/0143952 A1 | 5/2017 | Siess et al. |
| 2017/0157309 A1 | 6/2017 | Begg et al. |
| 2017/0209633 A1 | 7/2017 | Cohen |
| 2017/0274128 A1 | 9/2017 | Tamburino et al. |
| 2017/0333607 A1 | 11/2017 | Zarins |
| 2017/0333608 A1 | 11/2017 | Zeng |
| 2017/0340787 A1 | 11/2017 | Corbett et al. |
| 2017/0340788 A1 | 11/2017 | Korakianitis et al. |
| 2017/0340789 A1 | 11/2017 | Bonde et al. |
| 2018/0015214 A1 | 1/2018 | Lynch |
| 2018/0021494 A1 | 1/2018 | Muller et al. |
| 2018/0021495 A1 | 1/2018 | Muller et al. |
| 2018/0050141 A1 | 2/2018 | Corbett et al. |
| 2018/0055979 A1 | 3/2018 | Corbett et al. |
| 2018/0064860 A1 | 3/2018 | Nunez et al. |
| 2018/0099076 A1 | 4/2018 | LaRose |
| 2018/0110907 A1 | 4/2018 | Keenan et al. |
| 2018/0133379 A1 | 5/2018 | Farnan et al. |
| 2018/0154058 A1 | 6/2018 | Menon et al. |
| 2018/0169312 A1 | 6/2018 | Barry |
| 2018/0169313 A1 | 6/2018 | Schwammenthal et al. |
| 2018/0207336 A1 | 7/2018 | Solem |
| 2018/0221551 A1 | 8/2018 | Tanner et al. |
| 2018/0221553 A1 | 8/2018 | Taskin |
| 2018/0228950 A1 | 8/2018 | Janeczek et al. |
| 2018/0228953 A1 | 8/2018 | Siess et al. |
| 2018/0243004 A1 | 8/2018 | Von Segesser et al. |

(56) References Cited

U.S. PATENT DOCUMENTS

| | | |
|---|---|---|
| 2018/0250456 A1 | 9/2018 | Nitzan et al. |
| 2018/0280598 A1 | 10/2018 | Curran et al. |
| 2018/0289877 A1 | 10/2018 | Schumacher et al. |
| 2018/0303990 A1 | 10/2018 | Siess et al. |
| 2018/0311423 A1 | 11/2018 | Zeng et al. |
| 2018/0318483 A1 | 11/2018 | Dague et al. |
| 2018/0318547 A1 | 11/2018 | Yokoyama |
| 2018/0326132 A1 | 11/2018 | Maimon et al. |
| 2018/0335037 A1 | 11/2018 | Shambaugh et al. |
| 2018/0345028 A1 | 12/2018 | Aboud et al. |
| 2018/0361042 A1 | 12/2018 | Fitzgerald et al. |
| 2018/0369469 A1 | 12/2018 | Le Duc De Lillers et al. |
| 2019/0001034 A1 | 1/2019 | Taskin et al. |
| 2019/0004037 A1 | 1/2019 | Zhang et al. |
| 2019/0030228 A1 | 1/2019 | Keenan et al. |
| 2019/0046702 A1 | 2/2019 | Siess et al. |
| 2019/0046703 A1* | 2/2019 | Shambaugh .......... A61M 60/81 |
| 2019/0054223 A1 | 2/2019 | Frazier et al. |
| 2019/0060539 A1 | 2/2019 | Siess et al. |
| 2019/0060543 A1 | 2/2019 | Khanal et al. |
| 2019/0076167 A1 | 3/2019 | Fantuzzi et al. |
| 2019/0083690 A1 | 3/2019 | Siess et al. |
| 2019/0099532 A1 | 4/2019 | Er |
| 2019/0101130 A1 | 4/2019 | Bredenbreuker et al. |
| 2019/0105437 A1 | 4/2019 | Siess et al. |
| 2019/0117865 A1 | 4/2019 | Walters et al. |
| 2019/0125948 A1 | 5/2019 | Stanfield et al. |
| 2019/0143016 A1 | 5/2019 | Corbett et al. |
| 2019/0143018 A1 | 5/2019 | Salahieh et al. |
| 2019/0154053 A1 | 5/2019 | McBride et al. |
| 2019/0167875 A1 | 6/2019 | Simon et al. |
| 2019/0167878 A1 | 6/2019 | Rowe |
| 2019/0170153 A1 | 6/2019 | Scheckel |
| 2019/0175806 A1 | 6/2019 | Tuval et al. |
| 2019/0184078 A1 | 6/2019 | Zilbershlag et al. |
| 2019/0184080 A1 | 6/2019 | Mohl |
| 2019/0192752 A1 | 6/2019 | Tiller et al. |
| 2019/0201603 A1 | 7/2019 | Siess et al. |
| 2019/0209755 A1 | 7/2019 | Nix et al. |
| 2019/0209758 A1 | 7/2019 | Tuval et al. |
| 2019/0211836 A1 | 7/2019 | Schumacher et al. |
| 2019/0211846 A1 | 7/2019 | Liebing |
| 2019/0223877 A1 | 7/2019 | Nitzen et al. |
| 2019/0269840 A1 | 9/2019 | Tuval et al. |
| 2019/0275224 A1 | 9/2019 | Hanson et al. |
| 2019/0282741 A1 | 9/2019 | Franano et al. |
| 2019/0282744 A1 | 9/2019 | D'Ambrosio et al. |
| 2019/0290817 A1 | 9/2019 | Guo et al. |
| 2019/0298902 A1 | 10/2019 | Siess et al. |
| 2019/0316591 A1 | 10/2019 | Toellner |
| 2019/0321527 A1 | 10/2019 | King et al. |
| 2019/0321529 A1 | 10/2019 | Korakianitis et al. |
| 2019/0321531 A1 | 10/2019 | Cambronne et al. |
| 2019/0336664 A1 | 11/2019 | Liebing |
| 2019/0344000 A1 | 11/2019 | Kushwaha et al. |
| 2019/0344001 A1 | 11/2019 | Salahieh et al. |
| 2019/0351117 A1 | 11/2019 | Cambronne et al. |
| 2019/0351119 A1 | 11/2019 | Cambronne et al. |
| 2019/0351120 A1 | 11/2019 | Kushwaha et al. |
| 2019/0358378 A1 | 11/2019 | Schumacher |
| 2019/0358379 A1 | 11/2019 | Wiessler et al. |
| 2019/0358384 A1 | 11/2019 | Epple |
| 2019/0365975 A1 | 12/2019 | Muller et al. |
| 2019/0383298 A1 | 12/2019 | Toellner |
| 2020/0016309 A1 | 1/2020 | Kallenbach et al. |
| 2020/0023109 A1 | 1/2020 | Epple |
| 2020/0030507 A1 | 1/2020 | Higgins et al. |
| 2020/0030509 A1 | 1/2020 | Siess et al. |
| 2020/0030510 A1 | 1/2020 | Higgins |
| 2020/0030511 A1 | 1/2020 | Higgins |
| 2020/0030512 A1 | 1/2020 | Higgins et al. |
| 2020/0038567 A1 | 2/2020 | Siess et al. |
| 2020/0038568 A1 | 2/2020 | Higgins et al. |
| 2020/0038571 A1 | 2/2020 | Jahangir |
| 2020/0069857 A1 | 3/2020 | Schwammenthal et al. |
| 2020/0088207 A1 | 3/2020 | Schumacher et al. |
| 2020/0114053 A1 | 4/2020 | Salahieh et al. |
| 2020/0129684 A1 | 4/2020 | Pfeffer et al. |
| 2020/0139028 A1 | 5/2020 | Scheckel et al. |
| 2020/0139029 A1 | 5/2020 | Scheckel et al. |
| 2020/0147283 A1 | 5/2020 | Tanner et al. |
| 2020/0164125 A1 | 5/2020 | Muller et al. |
| 2020/0164126 A1 | 5/2020 | Muller |
| 2020/0345337 A1 | 11/2020 | Muller et al. |
| 2020/0350812 A1 | 11/2020 | Vogt et al. |
| 2021/0052793 A1 | 2/2021 | Struthers et al. |
| 2021/0268264 A1 | 9/2021 | Stotz |
| 2021/0290929 A1 | 9/2021 | Stotz |
| 2021/0290930 A1 | 9/2021 | Kasel |
| 2021/0290932 A1 | 9/2021 | Stotz |
| 2021/0290937 A1 | 9/2021 | Baumbach |
| 2021/0313869 A1 | 10/2021 | Strasswiemer et al. |
| 2021/0316133 A1 | 10/2021 | Kassel et al. |
| 2021/0322756 A1 | 10/2021 | Vollmer et al. |
| 2021/0330958 A1 | 10/2021 | Stotz et al. |
| 2021/0338999 A1 | 11/2021 | Stotz et al. |
| 2021/0339004 A1 | 11/2021 | Schlebusch et al. |
| 2021/0339005 A1 | 11/2021 | Stotz et al. |
| 2021/0346678 A1 | 11/2021 | Baumbach et al. |
| 2021/0346680 A1 | 11/2021 | Vogt et al. |
| 2021/0379352 A1 | 12/2021 | Schlebusch et al. |
| 2021/0379355 A1 | 12/2021 | Schuelke et al. |
| 2021/0379358 A1 | 12/2021 | Schuelke et al. |
| 2021/0384812 A1 | 12/2021 | Vollmer et al. |
| 2022/0008714 A1 | 1/2022 | Stotz |
| 2022/0016411 A1 | 1/2022 | Winterwerber |
| 2022/0072296 A1 | 3/2022 | Mori |
| 2022/0072297 A1 | 3/2022 | Tuval et al. |
| 2022/0080178 A1 | 3/2022 | Salahieh et al. |
| 2022/0080180 A1 | 3/2022 | Siess et al. |
| 2022/0080182 A1 | 3/2022 | Earles et al. |
| 2022/0080183 A1 | 3/2022 | Earles et al. |
| 2022/0080184 A1 | 3/2022 | Clifton et al. |
| 2022/0080185 A1 | 3/2022 | Clifton et al. |
| 2022/0105337 A1 | 4/2022 | Salahieh et al. |
| 2022/0105339 A1 | 4/2022 | Nix et al. |
| 2022/0126083 A1 | 4/2022 | Grauwinkel et al. |
| 2022/0161018 A1 | 5/2022 | Mitze et al. |
| 2022/0161019 A1 | 5/2022 | Mitze et al. |
| 2022/0161021 A1 | 5/2022 | Mitze et al. |
| 2022/0241580 A1* | 8/2022 | Stotz .................. A61M 60/126 |
| 2023/0001178 A1 | 1/2023 | Corbett et al. |
| 2023/0277836 A1 | 9/2023 | Schellenberg et al. |
| 2023/0293878 A1 | 9/2023 | Christof et al. |

FOREIGN PATENT DOCUMENTS

| | | |
|---|---|---|
| AU | 2012261669 | 1/2013 |
| AU | 2013203301 | 5/2013 |
| AU | 2013273663 | 1/2014 |
| BR | PI0904483-3 | 7/2011 |
| CA | 2 026 692 | 4/1992 |
| CA | 2 026 693 | 4/1992 |
| CA | 2 796 357 | 10/2011 |
| CA | 2 947 984 | 11/2022 |
| CN | 1222862 A | 7/1999 |
| CN | 1254598 A | 5/2000 |
| CN | 1376523 A | 10/2002 |
| CN | 2535055 | 2/2003 |
| CN | 1118304 C | 8/2003 |
| CN | 2616217 | 5/2004 |
| CN | 1202871 C | 5/2005 |
| CN | 1833736 A | 9/2006 |
| CN | 200977306 | 11/2007 |
| CN | 101112628 | 1/2008 |
| CN | 201150675 | 11/2008 |
| CN | 201437016 | 4/2010 |
| CN | 201618200 | 11/2010 |
| CN | 201658687 | 12/2010 |
| CN | 201710717 | 1/2011 |
| CN | 201894758 | 7/2011 |
| CN | 102475923 | 5/2012 |
| CN | 102545538 | 7/2012 |
| CN | 202314596 | 7/2012 |

(56) References Cited

FOREIGN PATENT DOCUMENTS

| | | |
|---|---|---|
| CN | 102743801 | 10/2012 |
| CN | 103143072 | 6/2013 |
| CN | 103845766 | 6/2014 |
| CN | 103861162 | 6/2014 |
| CN | 203842087 | 9/2014 |
| CN | 104208763 | 12/2014 |
| CN | 104208764 | 12/2014 |
| CN | 203971004 | 12/2014 |
| CN | 104274873 | 1/2015 |
| CN | 204106671 | 1/2015 |
| CN | 204219479 | 3/2015 |
| CN | 103877630 | 2/2016 |
| CN | 205215814 | 5/2016 |
| CN | 103977464 | 8/2016 |
| CN | 104162192 | 9/2016 |
| CN | 104888293 | 3/2017 |
| CN | 106512117 | 3/2017 |
| CN | 104225696 | 6/2017 |
| CN | 107019824 | 8/2017 |
| CN | 206443963 | 8/2017 |
| CN | 107281567 | 10/2017 |
| CN | 104707194 | 11/2017 |
| CN | 105498002 | 6/2018 |
| CN | 106310410 | 7/2018 |
| CN | 106902404 | 8/2019 |
| CN | 209790495 | 12/2019 |
| CN | 110665079 | 1/2020 |
| CN | 210020563 | 2/2020 |
| CN | 111166948 | 5/2020 |
| CN | 111166949 | 5/2020 |
| DE | 1 001 642 | 1/1957 |
| DE | 1 165 144 | 3/1964 |
| DE | 26 24 058 | 12/1977 |
| DE | 3 545 214 | 7/1986 |
| DE | 195 46 336 | 5/1997 |
| DE | 695 01 834 | 10/1998 |
| DE | 198 54 724 | 5/1999 |
| DE | 198 21 307 | 10/1999 |
| DE | 199 10 872 | 10/1999 |
| DE | 199 56 380 | 11/1999 |
| DE | 100 59 714 | 5/2002 |
| DE | 101 55 011 | 11/2005 |
| DE | 601 19 592 | 9/2006 |
| DE | 20 2005 020 288 | 6/2007 |
| DE | 10 2008 060 357 | 6/2010 |
| DE | 10 2009 039 658 | 3/2011 |
| DE | 20 2009 018 416 | 8/2011 |
| DE | 10 2012 022 456 | 5/2014 |
| DE | 10 2013 007 562 | 11/2014 |
| DE | 10 2014 210 299 | 12/2015 |
| DE | 10 2014 212 323 | 12/2015 |
| DE | 11 2014 001 418 | 12/2015 |
| DE | 10 2014 224 151 | 6/2016 |
| DE | 20 2015 009 422 | 7/2017 |
| DE | 10 2012 207 042 | 9/2017 |
| DE | 10 2016 013 334 | 4/2018 |
| DE | 10 2017 212 193 | 1/2019 |
| DE | 10 2018 207 611 | 11/2019 |
| DE | 10 2018 208 945 | 12/2019 |
| DE | 10 2018 211 327 | 1/2020 |
| DE | 10 2018 212 153 | 1/2020 |
| DE | 10 2018 213 350 | 2/2020 |
| DE | 11 2020 003 063 | 3/2022 |
| DE | 11 2020 004 148 | 6/2022 |
| EP | 0 050 814 | 5/1982 |
| EP | 0 629 412 | 12/1994 |
| EP | 0 764 448 | 3/1997 |
| EP | 0 855 515 | 7/1998 |
| EP | 0 890 179 | 1/1999 |
| EP | 1 013 294 | 6/2000 |
| EP | 1 186 873 | 3/2002 |
| EP | 1 475 880 | 11/2004 |
| EP | 1 169 072 | 5/2005 |
| EP | 1 176 999 | 7/2005 |
| EP | 1 801 420 | 6/2007 |
| EP | 2 009 233 | 12/2008 |
| EP | 2 098 746 | 9/2009 |
| EP | 2 403 109 | 1/2012 |
| EP | 2 187 807 | 6/2012 |
| EP | 3 326 567 | 10/2014 |
| EP | 1 898 971 | 3/2015 |
| EP | 2 519 273 | 8/2015 |
| EP | 2 438 936 | 10/2015 |
| EP | 2 438 937 | 10/2015 |
| EP | 2 960 515 | 12/2015 |
| EP | 2 968 718 | 1/2016 |
| EP | 1 996 252 | 5/2016 |
| EP | 2 475 415 | 6/2016 |
| EP | 2 906 265 | 7/2016 |
| EP | 3 069 739 | 9/2016 |
| EP | 3 127 562 | 2/2017 |
| EP | 2 585 129 | 3/2017 |
| EP | 3 222 301 | 9/2017 |
| EP | 3 222 302 | 9/2017 |
| EP | 3 020 426 | 12/2017 |
| EP | 3 038 669 | 1/2018 |
| EP | 3 062 730 | 1/2018 |
| EP | 3 180 050 | 2/2018 |
| EP | 3 287 154 | 2/2018 |
| EP | 1 789 129 | 6/2018 |
| EP | 2 366 412 | 8/2018 |
| EP | 3 205 359 | 8/2018 |
| EP | 3 205 360 | 8/2018 |
| EP | 3 456 367 | 3/2019 |
| EP | 3 119 451 | 6/2019 |
| EP | 3 542 835 | 9/2019 |
| EP | 3 542 836 | 9/2019 |
| EP | 3 711 785 | 9/2020 |
| EP | 3 711 786 | 9/2020 |
| EP | 3 711 787 | 9/2020 |
| EP | 3 142 722 | 12/2020 |
| EP | 3 579 894 | 12/2020 |
| EP | 3 188 769 | 1/2021 |
| EP | 3 490 122 | 1/2021 |
| EP | 2 869 866 | 2/2021 |
| EP | 3 398 626 | 2/2021 |
| EP | 3 487 549 | 2/2021 |
| EP | 3 113 806 | 3/2021 |
| EP | 3 615 103 | 3/2021 |
| EP | 2 344 218 | 4/2021 |
| EP | 3 436 104 | 4/2021 |
| EP | 3 749 383 | 4/2021 |
| EP | 3 131 615 | 6/2021 |
| EP | 3 338 825 | 6/2021 |
| EP | 3 432 944 | 6/2021 |
| EP | 3 684 439 | 7/2021 |
| EP | 2 582 414 | 8/2021 |
| EP | 3 407 930 | 8/2021 |
| EP | 3 782 665 | 8/2021 |
| EP | 3 782 666 | 8/2021 |
| EP | 3 782 668 | 8/2021 |
| EP | 3 858 397 | 8/2021 |
| EP | 3 216 467 | 9/2021 |
| EP | 3 884 968 | 9/2021 |
| EP | 3 884 969 | 9/2021 |
| EP | 3 027 241 | 10/2021 |
| EP | 3 579 904 | 11/2021 |
| EP | 2 628 493 | 12/2021 |
| EP | 3 556 409 | 1/2022 |
| EP | 3 624 868 | 1/2022 |
| EP | 3 624 867 | 3/2022 |
| EP | 3 689 389 | 3/2022 |
| EP | 3 697 464 | 3/2022 |
| EP | 3 737 436 | 3/2022 |
| EP | 3 972 661 | 3/2022 |
| EP | 2 967 630 | 4/2022 |
| EP | 3 142 721 | 4/2022 |
| EP | 3 520 834 | 4/2022 |
| EP | 3 586 887 | 4/2022 |
| EP | 3 638 336 | 4/2022 |
| EP | 3 689 388 | 4/2022 |
| EP | 3 765 110 | 4/2022 |
| EP | 3 782 667 | 4/2022 |
| EP | 3 829 673 | 4/2022 |

(56) References Cited

FOREIGN PATENT DOCUMENTS

| | | |
|---|---|---|
| EP | 3 976 129 | 4/2022 |
| EP | 3 984 589 | 4/2022 |
| EP | 3 986 528 | 4/2022 |
| EP | 3 649 926 | 5/2022 |
| EP | 3 653 113 | 5/2022 |
| EP | 3 654 006 | 5/2022 |
| EP | 3 735 280 | 5/2022 |
| EP | 3 897 814 | 5/2022 |
| EP | 3 219 339 | 6/2022 |
| EP | 3 737 310 | 7/2022 |
| EP | 3 899 994 | 8/2022 |
| EP | 3 487 550 | 9/2022 |
| EP | 3 606 575 | 9/2022 |
| EP | 3 834 876 | 9/2022 |
| EP | 3 000 492 | 10/2022 |
| EP | 3 600 477 | 10/2022 |
| EP | 3 897 768 | 10/2022 |
| EP | 3 914 310 | 10/2022 |
| EP | 3 914 311 | 10/2022 |
| EP | 3 000 493 | 11/2022 |
| EP | 3 858 422 | 11/2022 |
| EP | 3 866 876 | 11/2022 |
| EP | 3 941 546 | 11/2022 |
| EP | 2 892 583 | 1/2023 |
| EP | 3 393 542 | 1/2023 |
| EP | 3 597 231 | 1/2023 |
| EP | 3 656 292 | 1/2023 |
| EP | 3 768 345 | 1/2023 |
| EP | 2 868 332 | 2/2023 |
| EP | 3 003 420 | 2/2023 |
| EP | 3 539 585 | 2/2023 |
| EP | 3 956 010 | 2/2023 |
| EP | 3 046 594 | 3/2023 |
| EP | 3 127 563 | 3/2023 |
| EP | 3 256 186 | 3/2023 |
| EP | 3 288 609 | 3/2023 |
| EP | 3 538 173 | 3/2023 |
| EP | 3 606 576 | 3/2023 |
| EP | 3 927 390 | 3/2023 |
| EP | 3 384 940 | 4/2023 |
| EP | 3 441 616 | 4/2023 |
| EP | 3 938 005 | 4/2023 |
| EP | 3 946 511 | 4/2023 |
| EP | 3 544 649 | 6/2023 |
| EP | 3 634 528 | 6/2023 |
| EP | 3 912 673 | 7/2023 |
| FR | 1458525 | 3/1966 |
| GB | 0 648 739 | 1/1951 |
| GB | 2 213 541 | 8/1989 |
| GB | 2 345 387 | 7/2000 |
| GB | 2 451 161 | 12/2011 |
| GB | 2 545 062 | 6/2017 |
| GB | 2 545 750 | 6/2017 |
| JP | 59-119788 | 8/1984 |
| JP | S61-500059 | 1/1986 |
| JP | S62-113555 | 7/1987 |
| JP | S64-68236 | 3/1989 |
| JP | H02-055886 | 2/1990 |
| JP | 2-79738 | 3/1990 |
| JP | H04-176471 | 6/1992 |
| JP | H04-108384 | 9/1992 |
| JP | H08-057042 | 3/1996 |
| JP | H10-052489 | 2/1998 |
| JP | 2888609 | 5/1999 |
| JP | 2889384 | 5/1999 |
| JP | H11-239617 | 9/1999 |
| JP | 2001-037728 | 2/2001 |
| JP | 2001-515375 | 9/2001 |
| JP | 2003-019197 | 1/2003 |
| JP | 2004-278375 | 10/2004 |
| JP | 2005-028137 | 2/2005 |
| JP | 2008-511414 | 4/2008 |
| JP | 2008-516654 | 5/2008 |
| JP | 2010-518907 | 6/2010 |
| JP | 2010-258181 | 11/2010 |
| JP | 2010-534080 | 11/2010 |
| JP | 2013-013216 | 1/2013 |
| JP | 2013-519497 | 5/2013 |
| JP | 2014-004303 | 1/2014 |
| JP | 2014-524274 | 9/2014 |
| JP | 2015-514529 | 5/2015 |
| JP | 2015-514531 | 5/2015 |
| JP | 2015-122448 | 7/2015 |
| JP | 2016-002466 | 1/2016 |
| JP | 2016-532500 | 10/2016 |
| JP | 6267625 | 1/2018 |
| JP | 6572056 | 9/2019 |
| JP | 2020-072985 | 5/2020 |
| JP | 2018-510708 | 3/2021 |
| KR | 10-2011-0098192 | 9/2011 |
| RO | 131676 | 2/2017 |
| RU | 2 051 695 | 1/1996 |
| TW | 374317 | 11/1999 |
| WO | WO 94/009835 | 5/1994 |
| WO | WO 97/037696 | 10/1997 |
| WO | WO 97/039785 | 10/1997 |
| WO | WO 99/049912 | 10/1999 |
| WO | WO 00/033446 | 6/2000 |
| WO | WO 02/022200 | 3/2002 |
| WO | WO 02/041935 | 5/2002 |
| WO | WO 02/070039 | 9/2002 |
| WO | WO 03/075981 | 9/2003 |
| WO | WO 03/103745 | 12/2003 |
| WO | WO 2005/020848 | 3/2005 |
| WO | WO 2005/028014 | 3/2005 |
| WO | WO 2005/037345 | 4/2005 |
| WO | WO 2007/033933 | 3/2007 |
| WO | WO 2007/105842 | 9/2007 |
| WO | WO 2008/017289 | 2/2008 |
| WO | WO 2008/081783 | 7/2008 |
| WO | WO 2009/010888 | 1/2009 |
| WO | WO 2009/046789 | 4/2009 |
| WO | WO 2009/046790 | 4/2009 |
| WO | WO 2009/073037 | 6/2009 |
| WO | WO 2010/119267 | 10/2010 |
| WO | WO 2011/003043 | 1/2011 |
| WO | WO 2011/081626 | 7/2011 |
| WO | WO 2011/160858 | 12/2011 |
| WO | WO 2012/018917 | 2/2012 |
| WO | WO 2012/047540 | 4/2012 |
| WO | WO 2012/112129 | 8/2012 |
| WO | WO 2013/037380 | 3/2013 |
| WO | WO 2013/120957 | 8/2013 |
| WO | WO 2013/167432 | 11/2013 |
| WO | WO 2013/173239 | 11/2013 |
| WO | WO 2015/039605 | 3/2015 |
| WO | WO 2015/063281 | 5/2015 |
| WO | WO 2015/085076 | 6/2015 |
| WO | WO 2015/109028 | 7/2015 |
| WO | WO 2015/172173 | 11/2015 |
| WO | WO 2015/175718 | 11/2015 |
| WO | WO 2016/028644 | 2/2016 |
| WO | WO 2016/137743 | 9/2016 |
| WO | WO 2016/146661 | 9/2016 |
| WO | WO 2016/146663 | 9/2016 |
| WO | WO 2017/004175 | 1/2017 |
| WO | WO 2017/015764 | 2/2017 |
| WO | WO 2017/021465 | 2/2017 |
| WO | WO 2017/053988 | 3/2017 |
| WO | WO 2017/060257 | 4/2017 |
| WO | WO 2017/112695 | 6/2017 |
| WO | WO 2017/112698 | 6/2017 |
| WO | WO 2017/147291 | 8/2017 |
| WO | WO 2017/159849 | 9/2017 |
| WO | WO 2017/162619 | 9/2017 |
| WO | WO 2017/205909 | 12/2017 |
| WO | WO 2018/088939 | 3/2018 |
| WO | WO 2018/109038 | 6/2018 |
| WO | WO 2018/139508 | 8/2018 |
| WO | WO 2018/197306 | 11/2018 |
| WO | WO 2019/034670 | 2/2019 |
| WO | WO 2019/035804 | 2/2019 |
| WO | WO 2019/038343 | 2/2019 |
| WO | WO 2019/057636 | 3/2019 |

(56) References Cited

FOREIGN PATENT DOCUMENTS

| | | |
|---|---|---|
| WO | WO 2019/078723 | 4/2019 |
| WO | WO 2019/135767 | 7/2019 |
| WO | WO 2019/137911 | 7/2019 |
| WO | WO 2019/138350 | 7/2019 |
| WO | WO 2019/145253 | 8/2019 |
| WO | WO 2019/158996 | 8/2019 |
| WO | WO 2019/161245 | 8/2019 |
| WO | WO 2019/180104 | 9/2019 |
| WO | WO 2019/180179 | 9/2019 |
| WO | WO 2019/180181 | 9/2019 |
| WO | WO 2018/135477 | 11/2019 |
| WO | WO 2018/135478 | 11/2019 |
| WO | WO 2019/211410 | 11/2019 |
| WO | WO 2019/219868 | 11/2019 |
| WO | WO 2019/219871 | 11/2019 |
| WO | WO 2019/219872 | 11/2019 |
| WO | WO 2019/219874 | 11/2019 |
| WO | WO 2019/219876 | 11/2019 |
| WO | WO 2019/219881 | 11/2019 |
| WO | WO 2019/219882 | 11/2019 |
| WO | WO 2019/219883 | 11/2019 |
| WO | WO 2019/219884 | 11/2019 |
| WO | WO 2019/219885 | 11/2019 |
| WO | WO 2019/229210 | 12/2019 |
| WO | WO 2019/229211 | 12/2019 |
| WO | WO 2019/229214 | 12/2019 |
| WO | WO 2019/229220 | 12/2019 |
| WO | WO 2019/229221 | 12/2019 |
| WO | WO 2019/229222 | 12/2019 |
| WO | WO 2019/229223 | 12/2019 |
| WO | WO 2019/234146 | 12/2019 |
| WO | WO 2019/239259 | 12/2019 |
| WO | WO 2019/241556 | 12/2019 |
| WO | WO 2019/243582 | 12/2019 |
| WO | WO 2019/243588 | 12/2019 |
| WO | WO 2020/003110 | 1/2020 |
| WO | WO 2020/011760 | 1/2020 |
| WO | WO 2020/011795 | 1/2020 |
| WO | WO 2020/011797 | 1/2020 |
| WO | WO 2020/016438 | 1/2020 |
| WO | WO 2020/028312 | 2/2020 |
| WO | WO 2020/028537 | 2/2020 |
| WO | WO 2020/030700 | 2/2020 |
| WO | WO 2020/064911 | 4/2020 |
| WO | WO 2020/073047 | 4/2020 |
| WO | WO 2020/132211 | 6/2020 |
| WO | WO 2020/187797 | 9/2020 |
| WO | WO 2020/219430 | 10/2020 |
| WO | WO 2020/234785 | 11/2020 |
| WO | WO 2020/242881 | 12/2020 |
| WO | WO 2021/046275 | 3/2021 |
| WO | WO 2021/062265 | 4/2021 |
| WO | WO 2021/067691 | 4/2021 |
| WO | WO 2021/119478 | 6/2021 |
| WO | WO 2021/150777 | 7/2021 |
| WO | WO 2021/152013 | 8/2021 |
| WO | WO 2022/056542 | 3/2022 |
| WO | WO 2022/063650 | 3/2022 |
| WO | WO 2022/072944 | 4/2022 |
| WO | WO 2022/076862 | 4/2022 |
| WO | WO 2022/076948 | 4/2022 |
| WO | WO 2022/109589 | 5/2022 |
| WO | WO 2022/109590 | 5/2022 |
| WO | WO 2022/109591 | 5/2022 |
| WO | WO 2023/278599 | 1/2023 |
| WO | WO 2023/014742 | 2/2023 |
| WO | WO 2023/049813 | 3/2023 |
| WO | WO 2023/076869 | 5/2023 |

OTHER PUBLICATIONS

Vollkron et al., "Advanced Suction Detection for an Axial Flow Pump", Artificial Organs, 2006, vol. 30, No. 9, pp. 665-670.

Vollkron et al., "Development of a Suction Detection System for Axial Blood Pumps", Artificial Organs, 2004, vol. 28, No. 8, pp. 709-716.

* cited by examiner

PUMP FOR DELIVERING A FLUID AND METHOD OF MANUFACTURING A PUMP

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57. For example, this application claims the benefit of priority to German patent application number 102020102474.6, entitled PUMP FOR DELIVERING A FLUID AND METHOD OF MANUFACTURING A PUMP, and filed Jan. 31, 2020, the disclosure of which is hereby incorporated by reference herein in its entirety for all purposes and forms a part of this specification.

BACKGROUND

Field

This disclosure relates generally to cardiac pumps, in particular to cardiac pumps with seals.

Description of the Related Art

Cardiovascular support systems, so-called "VAD" (Ventricular Assist Device) systems, are used to provide cardiovascular support for patients with heart failure. These systems perform a partial or complete pumping function for a blood flow through the heart. These systems are divided into temporary systems for short-term cardiac support and permanent systems. The temporary systems are used, among other things, to bridge the time until a suitable donor heart is available and can be implanted. The permanent systems are used for long-term residence on or in the patient. A component of such systems is a blood pump, typically a centrifugal pump in the form of a turbopump, which is driven by an integrated electric motor and generates the required blood flow by means of an impeller. Conventional pumps have deficient seals or systems that require complex procedures, such as purging. Improvements to these and other drawbacks of existing cardiac pumps are desirable.

SUMMARY OF CERTAIN INVENTIVE ASPECTS

The embodiments disclosed herein each have several aspects no single one of which is solely responsible for the disclosure's desirable attributes. Without limiting the scope of this disclosure, its more prominent features will now be briefly discussed. After considering this discussion, and particularly after reading the section entitled "Detailed Description," one will understand how the features of the embodiments described herein provide advantages over existing systems, devices and methods for cardiac pumps.

The following disclosure describes non-limiting examples of some embodiments. For instance, other embodiments of the disclosed systems and methods may or may not include the features described herein. Moreover, disclosed advantages and benefits can apply only to certain embodiments and should not be used to limit the disclosure.

Against the above background, the approaches presented here introduce a pump for delivering a fluid and a method for manufacturing a pump, further a device using this method, and also a corresponding computer program according to the main requirements. The measures listed in the dependent claims allow for advantageous further training and improvements of the device specified in the independent claims. The subject of the present approach is also a computer program.

The advantages that can be achieved with the approaches presented are that a pump is created whose shaft housing is protected from fluid ingress by using only one or very few sealing elements.

In one aspect, a pump for transferring a fluid has an impeller, a drive device with a shaft, a shaft housing and a sealing device. The impeller is designed to pump the fluid. The drive device with the shaft is designed to drive the impeller. The shaft housing is designed to accommodate the shaft and in addition or alternatively the drive device. The sealing device has at least one housing sealing element and additionally or alternatively an impeller sealing element which is accommodated between the drive device and the impeller and which is designed to prevent the fluid from entering the shaft housing and additionally or alternatively the drive device during operation of the pump.

The impeller can have a cylindrically shaped or tapered basic body, which is rotatable around a longitudinal axis during operation of the impeller. Radially around the longitudinal axis, the basic body can have one or more blades or vanes to create a fluid flow or fluid suction when the impeller rotates in the fluid. For this purpose the vane or vanes can be arranged spirally wound around an outer wall of the basic body. A body of revolution is typically created by the rotation of one or more so-called "B-Splines". In addition to the shaft, the drive device can have a motor coupled to the shaft, for example an electric motor. The shaft can be straight. The shaft housing can be tubular to accommodate at least part or all of the shaft or the entire drive unit with the motor. The housing sealing element and additionally or alternatively the impeller sealing element can be made of a solid, for example elastic, material. Thanks to the sealing device, fluid penetration into the shaft housing and additionally or alternatively the drive device is prevented or minimized during operation of the pump. It is advantageous to dispense with additional sealing media such as barrier media or flushing media.

The housing sealing element can be attached to an inner side of the shaft housing and can be arranged additionally or alternatively around the shaft. Thus, the sealing element can be arranged to seal the shaft against an inner side of the shaft housing to prevent or minimize the penetration of the fluid into the shaft housing. For example, the housing sealing element can be shaped as a sealing ring, especially a rotary shaft seal. According to one design, the casing sealing element can be attached to an inlet opening of the shaft casing facing the impeller in order to seal this inlet opening.

The impeller sealing element can be fixed to the impeller and additionally or alternatively arranged around the shaft and additionally or alternatively contacting the shaft housing. In this way the shaft can be sealed against the shaft housing in the axial direction. For example, the impeller sealing element can be designed as another sealing ring, in particular an axial shaft seal. The axial shaft seal can also be described as a "V-ring" and has a v-shaped or plate-shaped flexible sealing lip that extends away from an annular base body of the axial shaft seal. The sealing lip can be attached to the impeller.

The impeller sealing element can be preloaded towards the shaft in mounted condition. A preload can be achieved by a deformation of the impeller sealing element, for example, if the impeller sealing element has the previously described deformation of the axial shaft seal. However, the preload can also be effected by means of an additional spring element.

It is also advantageous if the impeller sealing element has, according to a design, at least one gap sealing element arranged to fluidically seal a gap between the shaft housing and the impeller to prevent the fluid from entering the gap. The gap sealing element can be an additional sealing ring. An outside diameter of the gap sealing element may be larger than an outside diameter of the impeller sealing element. A sealing effect in axial direction can be increased by an additional gap sealing element.

A free end of the shaft can be supported in the impeller. This creates a stable mechanical coupling between the shaft and the impeller. Alternatively, the free end of the shaft and the impeller can be connected contactlessly by means of a magnetic coupling.

According to one design, the pump can have a bearing device for radial, and additionally or alternatively, axial bearing of the shaft in the shaft housing. This bearing arrangement can be used to ensure stability of the shaft during operation of the pump.

A method for manufacturing a pump for delivering a fluid is also presented. The process includes a step of providing and a step of assembling. In the step of providing, an impeller for conveying the fluid, a drive means with a shaft designed to drive the impeller, a shaft housing for receiving the shaft and additionally or alternatively the drive means and a sealing means with at least one housing sealing element and additionally or alternatively, an impeller sealing element are provided as components. In the step of assembling the components are assembled to produce the pump, whereby in the step of assembling the housing sealing element and additionally or alternatively the impeller sealing element is accommodated between the drive device and the impeller in order to prevent or reduce fluid penetration into the shaft housing and additionally or alternatively the drive device during operation of the pump.

This procedure can be implemented in software or hardware, for example, or in a mixture of software and hardware in an ECU, for example.

The approach presented here also creates a device that is designed to perform, control, or implement the steps of a variant of a process presented here in appropriate facilities. Also, by this design variant of the approach in form of a device the task underlying the approach can be solved fast and efficiently.

For this purpose, the device can have at least one computing unit for processing signals or data, at least one memory unit for storing signals or data, at least one interface to a sensor or an actuator for reading in sensor signals from the sensor or for outputting data or control signals to the actuator and/or at least one communication interface for reading in or outputting data embedded in a communication protocol. The computing unit may be, for example, a signal processor, a microcontroller or the like, whereby the memory unit may be a flash memory, an EEPROM or a magnetic memory unit. The communication interface may be designed to read or output data wirelessly and/or wired, whereby a communication interface that can read or output wired data can, for example, read or output this data electrically or optically from a corresponding data transmission line or output it to a corresponding data transmission line.

A device can be understood as an electrical device that processes sensor signals and outputs control and/or data signals depending on them. The device can have an interface, which can be hardware and/or software based. In the case of a hardware-based design, the interfaces can be part of a so-called system ASIC, which contains various functions of the device. However, it is also possible that the interfaces are own integrated circuits or at least partly consist of discrete components. In the case of a software-based education, the interfaces can be software modules, which for example are available on a microcontroller next to other software modules.

A computer program product or computer program with program code, which may be stored on a machine-readable carrier or storage medium, such as a semiconductor memory, a hard disk memory or an optical memory, and which is used to carry out, implement and/or control the steps of the process according to one of the forms of execution described above, is also advantageous, in particular if the program product or program is executed on a computer or device.

BRIEF DESCRIPTION OF THE DRAWINGS

The foregoing and other features of the present disclosure will become more fully apparent from the following description and appended claims, taken in conjunction with the accompanying drawings. Understanding that these drawings depict only several embodiments in accordance with the disclosure and are not to be considered limiting of its scope, the disclosure will be described with additional specificity and detail through use of the accompanying drawings. In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the drawing, can be arranged, substituted, combined, and designed in a wide variety of different configurations, all of which are explicitly contemplated and make part of this disclosure.

Execution examples of the approaches presented here are shown in the drawings and explained in more detail in the following description. It shows.

While the above-identified drawings set forth presently disclosed embodiments, other embodiments are also contemplated, as noted in the discussion. This disclosure presents illustrative embodiments by way of representation and not limitation. Numerous other modifications and embodiments can be devised by those skilled in the art which fall within the scope and spirit of the principles of the presently disclosed embodiments.

DETAILED DESCRIPTION OF CERTAIN EMBODIMENTS

The following detailed description is directed to certain specific embodiments of the development. In this description, reference is made to the drawings wherein like parts or steps may be designated with like numerals throughout for clarity. Reference in this specification to "one embodiment," "an embodiment," or "in some embodiments" means that a particular feature, structure, or characteristic described in connection with the embodiment is included in at least one embodiment of the invention. Moreover, various features are described which may be exhibited by some embodiments and not by others. Similarly, various requirements are described which may be requirements for some embodiments but may not be requirements for other embodiments. Reference will now be made in detail to embodiments of the invention, examples of which are illustrated in the accompanying drawings. Wherever possible, the same reference numbers will be used throughout the drawings to refer to the same or like parts.

In the following description of favorable execution examples of the present approach, the same or similar reference signs are used for the elements represented in the different figures and which have a similar effect, whereby a repeated description of these elements is omitted.

Figure 1:
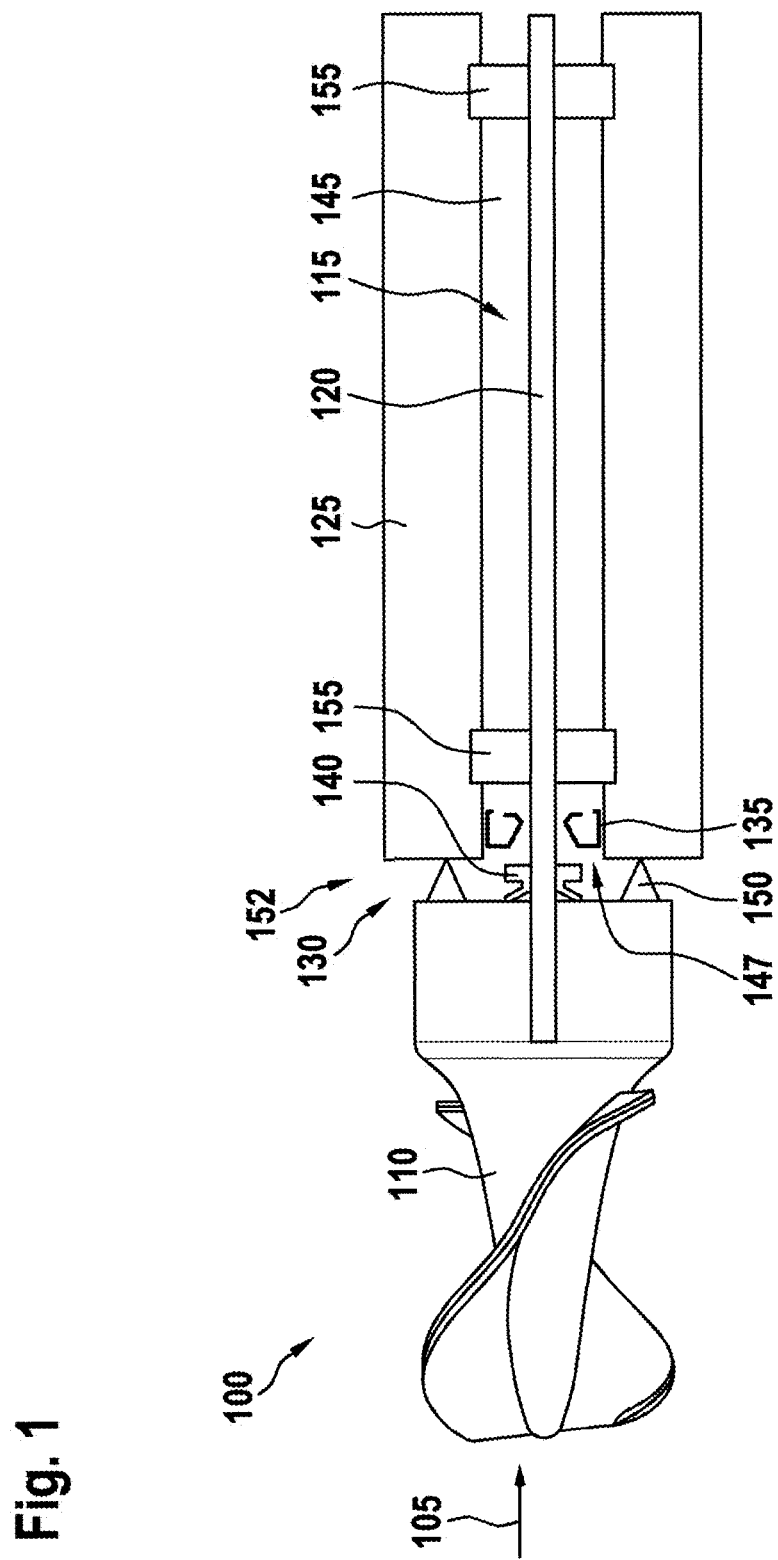
FIG. 1 is a schematic side view of a pump for pumping a fluid according to a design example.

FIG. 1 shows a schematic side view of a pump 100 for pumping a fluid 105 according to a design example. The pump 100 is designed and shaped for use in a fluid channel such as a blood vessel.

The pump 100 has an impeller 110, a drive device 115 with a shaft 120, a shaft housing 125 and a sealing device 130. The impeller 110 is designed to pump the fluid 105. The drive device 115 with shaft 120 is designed to drive the impeller 110. The shaft housing 125 is designed to accommodate the shaft 120 and/or the drive device 115 and is also referred to as the "housing" in the following. The sealing device 130 comprises at least one casing sealing element 135 and/or one impeller sealing element 140, which is accommodated between the drive device 115 and the impeller 110 and which is designed to prevent fluid 105 from entering the drive device 115 and/or the shaft casing 125 during operation of the pump 100.

According to this design example, the impeller 110 only has an exemplary tapered basic body, which can be rotated around a longitudinal axis during operation of the impeller 110. Radially around the longitudinal axis, the basic body according to this design example has two blades in order to generate a fluid flow or fluid suction in the fluid 105 when the impeller 110 rotates. For this purpose, the blades are arranged spirally wound around an outer wall of the basic body according to this design example. A body of rotation of the impeller 110 is created by the rotation of one or more so-called "B-spindles". According to an alternative design example, the impeller 110 has a differently shaped, for example cylindrical, basic body and/or a different number of blades or vanes. According to this design example, the drive unit 115, which will also be referred to as "drive" in the following, has a motor 145, for example in the form of an electric motor. According to this design example, the motor 145 is coupled to the shaft 120. The shaft 120 is straight according to this design example. The shaft housing 125 is correspondingly tubular according to this design example and accommodates at least the shaft 120 or, according to this design example, the entire drive unit 115 with the motor 145 completely. According to an alternative design example, the motor 145 is arranged outside the shaft housing 125. According to this design example, the housing sealing element 135 and/or impeller sealing element 140 is made of a strong but elastic material. In other words, the casing sealing element 135 and/or impeller sealing element 140 has no liquid or semi-liquid material.

According to this design example, the housing sealing element 135 is attached to an inner side of the shaft housing 125 and/or arranged around the shaft 120. According to this design example, the housing sealing element 135 is formed as a sealing ring, according to this design example as a rotary shaft seal. According to this design example, the casing sealing element 135 is attached to an inlet opening 147 of the shaft casing 125 facing the impeller 110. According to one design example, the casing sealing element 135 is fixed directly to the inlet opening 147.

The additional or alternative impeller sealing element 140 is attached to the impeller 110 and/or arranged around the shaft 120 and/or the shaft casing 125 in contact according to this design example. According to this design example, the impeller sealing element 140 is designed as an additional sealing ring, here an axial shaft seal. The axial shaft seal can also be described as a "V-ring". According to this design example, this V-ring has a V-shaped or plate-shaped flexible sealing lip that extends away from an annular base body of the axial shaft seal. According to this design example, the sealing lip is attached to the impeller 110.

The impeller sealing element 140 is also preloaded towards the shaft 120 in the mounted state according to this design example. A pretension is caused by a deformation of the impeller sealing element 140. According to an alternative design example, the pump 100 has a spring element which causes the preload.

Furthermore, according to this design example, the impeller sealing element 140 has at least one gap sealing element 150, which is arranged to fluidically seal a gap 152 between the shaft housing 125 and the impeller 110 in order to prevent the fluid 105 from entering the gap 152. According to this design example, the gap sealing element 150 is designed as an additional sealing ring. According to this design example, an outer diameter of the gap sealing element 150 is larger than an outer diameter of the impeller sealing element 140. According to this design example, the impeller sealing element 140 is arranged coaxially with respect to the additional sealing ring in a passage opening of the additional sealing ring.

A free end of the shaft 120 is fixed in the impeller 110 according to this design example. According to an alternative design example, the free end of the shaft 120 and the impeller 110 are connected without contact by means of a magnetic coupling, whereby a driving force of the motor 145 is magnetically transferable to the impeller 110.

The pump 100 also has, according to this design example, a bearing device 155 for radial and/or axial bearing of the shaft 120 in the shaft housing 125. For this purpose, the bearing device 155 according to this design example has two bearing elements at two opposite ends of an interior of the shaft housing 125, in which the shaft 120 is, for example, centrally mounted. According to this design example, the housing sealing element 135 is arranged outside a space bounded by the two bearing elements.

The pump 100 presented here can be used and shaped as a blood pump for a cardiac support system. According to one design example, the Pump 100 is designed as a VAD pump for short-term implantation with a contacting radial and/or axial seal.

For temporary/short-time used VAD-Pumps 100 it is important that they can be implanted very quickly. According to this design example, a system as simple as possible is used for this purpose. One of the tasks of the present approach is to use only one or more sealing elements 135, 140, 150 and to dispense with liquid or partially liquid media such as flushing media or barrier media or an external forced flushing for sealing.

According to this design example, the pump 100 presented here has the electric drive in the form of the electric motor 145, the rotating shaft 120, the impeller 110, the bearing device 155, the shaft housing 125 and at least one sealing element 135, 140, 150, which is firmly connected to the housing 125 according to a design example in the form of the housing sealing element 135 and has a sealing function with respect to the rotating shaft 120 and/or the impeller 110. Additionally or alternatively, the pump 100 has a sealing element in the form of the impeller sealing element 140 and/or gap sealing element 150, which seals the housing 125 against the rotating impeller 110 in the axial direction. According to this design example, the impeller 110 consists of a core with, for example, a hub and at least two or more blades. During operation of the pump 100, the fluid 105 is fed axially to the impeller 110 (suction) and discharged radially/diagonally through openings in an impeller housing of the impeller 110 not shown here. According to this design example, the impeller 110 is firmly connected to the drive shaft 120 of the motor 145, which provides the required drive power. According to this design example, the shaft 120 is supported by at least one radial and/or at least one axial bearing. Optionally, the bearings are also realized in combination with a radial-axial bearing. According to one possible design example, the housing 125 has at least one sealing element 135 to the impeller 110. According to another design example, this at least one sealing element 140, 150 is attached to the impeller 110. The seal is of contact design, i.e. according to one design example, the sealing element 135, 140 is always in contact with the shaft 120 and the casing 125. Furthermore, at least one (further) sealing element 140, which seals the shaft 120 against the casing 125, is arranged optionally/alternatively. This is designed according to a design example in such a way that the sealing element 140 is preloaded towards the shaft 120. According to one design example, this is realized with a spring or according to another design example, it is ensured by shaping the elastic sealing element 140. One possible design of the housing sealing element 135 is a rotary shaft seal. The axial shaft sealing ring is a possible design of the alternative/optional sealing element 140.

According to one design example, the VAD Pump 100 has a maximum outside diameter of less than five millimeters, in another design example it has an outside diameter of less than eight millimeters. According to one design example, the Pump 100 is designed for a short-term use of less than 24 hours, in another design example for a use of less than ten days, in another design example for less than 28 days and in another design example for less than or equal to six months.

Figure 2:
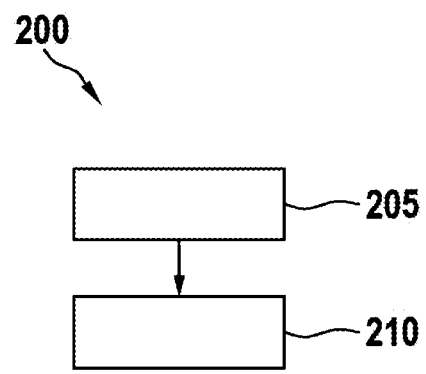
FIG. 2 is a flow chart of a process for manufacturing a pump for pumping a fluid according to a design example.

FIG. 2 shows a flowchart of a process 200 for manufacturing a pump for pumping a fluid according to a design example. This can be the pump described in FIG. 1.

Procedure 200 includes a 205 step of provisioning and a 210 step of assembly. In step 205 of providing, an impeller for conveying the fluid, a drive means with a shaft adapted to drive the impeller, a shaft housing for receiving the shaft and/or the drive means, and a sealing means with at least one housing sealing element and/or one impeller sealing element are provided. In the step 210 of assembling, the components are assembled to produce the pump, wherein in the step of assembling, the housing sealing element and/or the impeller sealing element is received between the drive means and the impeller to prevent fluid from entering the shaft housing and/or the drive means during operation of the pump.

According to a design example, in step 210 of the assembly process, the impeller is also connected to the shaft and/or the shaft and/or drive unit is mounted in the shaft housing in any order.

Figure 3:
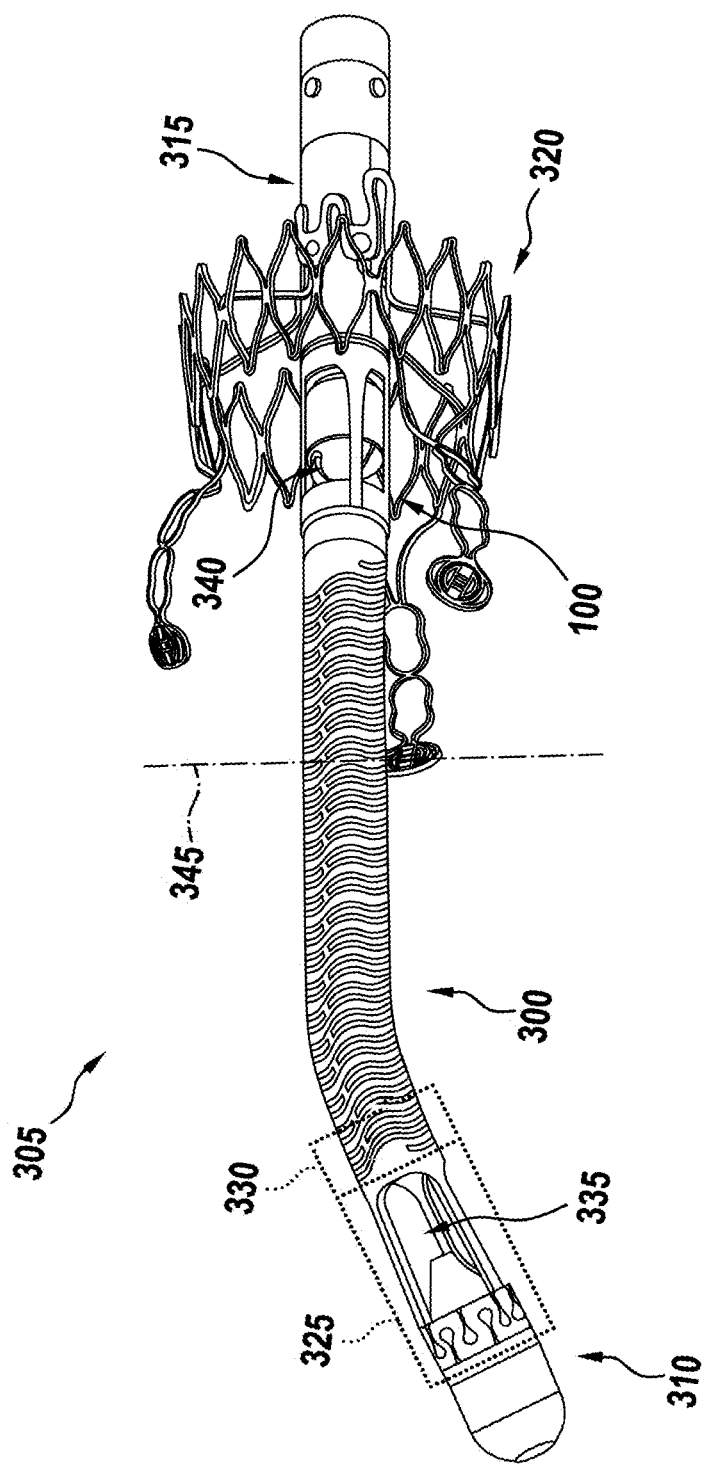
FIG. 3 is a perspective side view of a pump according to a design example.

FIG. 3 shows a perspective side view of a pump 100 according to an execution example. This can be an example of the pump 100 described in FIG. 1 or 2.

According to this design example, the pump 100 also has an inlet line 300 and is implemented as a cardiac support system 305, which is designed as a left ventricular assist device (LVAD) for positioning across an aortic valve. The elongated axial design of the Cardiac Support System 305 shown here with a substantially constant outer diameter allows transfemoral or transaortic implantation of the Cardiac Support System 305 for easy placement by means of a catheter in a blood vessel, such as the aorta. The inflow line 300 has an exemplary inclination of the longitudinal axis according to the shape for the aortic valve position and thus a slightly curved shape. The Cardiac Support System 305 comprises the inflow line 300, the pump 100, a head unit 310, a housing section 315 and an anchoring frame 320. The inlet line 300, which can also be called the "suction trunk", is located between the head unit 310 and the pump 100. The pump 100 is housed in the housing section 315, to which an optional anchoring frame 320 can be attached.

The inlet line 300 is designed according to a design example to direct a fluid flow to the pump 100 of the Cardiac Support System 305. According to this design example, the inlet line 300 comprises an inlet head section 325 and a contour section 330. The inlet head section 325 has at least one inlet opening 335 for introducing the fluid flow into the inlet line 300. The contour section 330 has an inner surface contour. The contour section 330 is arranged adjacent to the inlet head section 325. An inner diameter of contour section 330 is larger at a first position than the inner diameter at a second position. The inner surface contour has a fillet at the second position to reduce the inner diameter.

In the design example shown here, the feed head section 325 and the contour section 330 are marked as examples. Especially the contour section 330 optionally comprises a smaller or larger part of the feed line 300 than shown here. In the implanted state of the Cardiac Support System 305, the supply head section 325 and the contour section 330 are located in the left heart chamber. A further section of the supply line 300 is led through the aortic valve, and a section of the Cardiac Support System 305 with the pump 100 is located in a section of the aorta. A pump outlet 340 in the area of the pump 100 directs the fluid flow delivered through the inlet line 300 into the aorta. A marking 345 shows an example of a position of a heart valve, e.g. the aortic valve, through which the supply line 300 is passed in order to position the Cardiac Support System 305.

At least one inlet edge of the inlet opening 335 of the inlet head section 325 is rounded according to the design example shown here. In this example, the inlet opening 335 is designed as a window-shaped inlet cut into the inlet head section 325.

According to the design example shown here, a length of the contour section 330 corresponds to a radius of the feed line 300 within a tolerance range. The tolerance range means a maximum deviation of twenty percent from the radius of the feed line 300.

A cardiac support system limited in terms of installation space, such as the cardiac support system 305 shown here as an example, which can be implanted minimally invasively, has a comparatively low power consumption for a given pump efficiency. The efficiency is limited by the friction in the pump 100. The pressure loss or friction in the feed line 300 when conducting the fluid flow from the inlet port 335 of the feed head section 325 in the heart chamber to the pump 100 is adjustable by the shaping of the feed line 300. For this purpose, the inlet edges of the inlet opening 335 are rounded to reduce the pressure loss. This is the only way to prevent flow separation. The flow separation is suppressed by an inlet inner surface contour in the form of the contour section 330 formed according to the approach presented here, thus reducing the pressure loss.

If an execution example includes an "and/or" link between a first feature and a second feature, this should be read in such a way that the execution example has both the first feature and the second feature according to one execution form and either only the first feature or only the second feature according to another execution form.

Various modifications to the implementations described in this disclosure will be readily apparent to those skilled in the art, and the generic principles defined herein can be applied to other implementations without departing from the spirit or scope of this disclosure. Thus, the disclosure is not intended to be limited to the implementations shown herein, but is to be accorded the widest scope consistent with the claims, the principles and the novel features disclosed herein. The word "example" is used exclusively herein to mean "serving as an example, instance, or illustration." Any implementation described herein as "example" is not necessarily to be construed as preferred or advantageous over other implementations, unless otherwise stated.

Certain features that are described in this specification in the context of separate implementations also can be implemented in combination in a single implementation. Conversely, various features that are described in the context of a single implementation also can be implemented in multiple implementations separately or in any suitable sub-combination. Moreover, although features can be described above as acting in certain combinations and even initially claimed as such, one or more features from a claimed combination can in some cases be excised from the combination, and the claimed combination can be directed to a sub-combination or variation of a sub-combination.

Similarly, while operations are depicted in the drawings in a particular order, this should not be understood as requiring that such operations be performed in the particular order shown or in sequential order, or that all illustrated operations be performed, to achieve desirable results. Additionally, other implementations are within the scope of the following claims. In some cases, the actions recited in the claims can be performed in a different order and still achieve desirable results.

It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

What is claimed is:

1. A cardiac pump for delivering a fluid, the cardiac pump comprising:
    an impeller configured to convey the fluid;
    a drive comprising a shaft, wherein the shaft is configured to drive the impeller;
    a shaft housing configured to receive the shaft; and
    a seal comprising:
        at least one housing sealing element configured to be received between the shaft and the shaft housing and configured to prevent fluid from penetrating the shaft housing and the drive during operation of the cardiac pump;
        at least one impeller sealing element; and
        at least one gap sealing element, wherein the at least one gap sealing element is configured to be received between the shaft housing and the impeller and wherein an outer diameter of the gap sealing element is larger than an outer diameter of the impeller sealing element.

2. The cardiac pump according to claim 1, wherein the housing sealing element is fixed to an inner side of the shaft housing and is arranged around the shaft.

3. The cardiac pump according to claim 1, wherein the housing sealing element comprises a sealing ring.

4. The cardiac pump according to claim 1, wherein the housing sealing element is fixed to an inlet opening of the shaft housing arranged facing the shaft.

5. The cardiac pump according to claim 1, wherein the impeller sealing element is attached to and in contact with the impeller and arranged around the shaft.

6. The cardiac pump according to claim 1, wherein the impeller sealing element comprises a sealing ring.

7. The cardiac pump according to claim 1, wherein the impeller sealing element is preloaded towards the shaft when assembled.

8. The cardiac pump according to claim 1, wherein the seal comprises at least one gap sealing element configured to fluidically seal a gap between the shaft housing and the impeller, the gap sealing element being configured to prevent fluid from traversing the gap.

9. The cardiac pump according to claim 1, wherein a free end of the shaft is supported in the impeller.

10. The cardiac pump according to claim 1, further comprising a bearing configured to radially and/or axially support the shaft in the shaft housing.

11. A method of manufacturing a cardiac pump for delivering a fluid, the method comprising:
providing an impeller configured to convey the fluid, a drive device with a shaft configured to drive the impeller, a shaft housing configured to receive the shaft, and a sealing device comprising:
at least one housing sealing element:,
at least one impeller sealing element; and
at least one gap sealing element, wherein the at least one gap sealing element is configured to be received between the shaft housing and the impeller and wherein an outer diameter of the gap sealing element is larger than an outer diameter of the impeller sealing element; and
assembling the impeller, the drive device, the shaft housing, and the sealing device to produce the cardiac pump, wherein in the step of assembling the housing sealing element is received between the shaft and the shaft housing to prevent fluid from entering the shaft housing and/or the drive device during operation of the cardiac pump.

12. An apparatus configured to perform and/or control the steps of the method according to claim 11 in corresponding units.

13. A non-transitory computer-readable storage comprising instructions that, when executed, direct a processor to perform the method according to claim 11.

14. A cardiac pump for delivering a fluid, the cardiac pump comprising:
an impeller configured to convey the fluid;
a drive means comprising a shaft, wherein the shaft is configured to drive the impeller;
a shaft housing configured to receive the shaft; and
a sealing means comprising:
at least one housing sealing configured to be received between the shaft and the shaft housing and configured to prevent the fluid from penetrating the shaft housing and/or the drive means during operation of the cardiac pump;
at least one impeller sealing element; and
at least one gap sealing element, wherein the at least one gap sealing element is configured to be received between the shaft housing and the impeller and wherein an outer diameter of the gap sealing element is larger than an outer diameter of the impeller sealing element.

15. The cardiac pump according to claim 14, wherein the housing sealing element is fixed to an inner side of the shaft housing and/or is arranged around the shaft.

16. The cardiac pump according to claim 14, wherein the housing sealing element comprises a sealing ring.

17. The cardiac pump according to claim 14, wherein the housing sealing element is fixed to an inlet opening of the shaft housing arranged facing the shaft.

18. The cardiac pump according to claim 14, wherein the impeller sealing element is attached to and/or in contact with the impeller around the shaft and/or the shaft housing.

19. The cardiac pump according to claim 14, wherein the impeller sealing element comprises a sealing ring.

20. The cardiac pump according to claim 14, wherein the impeller sealing element is preloaded towards the shaft when assembled.

* * * * *